(12) United States Patent
Medina et al.

(10) Patent No.: US 8,578,082 B2
(45) Date of Patent: Nov. 5, 2013

(54) CONFIGURABLE PATIENT MONITORING SYSTEM

(75) Inventors: Casey Medina, Westminster, CO (US); Christopher Cagle, Arvada, CO (US); Wanran Ma, Boulder, CO (US)

(73) Assignee: Covidien LLP, Mansfield, MA (US)

( * ) Notice: Subject to any disclaimer, the term of this patent is extended or adjusted under 35 U.S.C. 154(b) by 179 days.

(21) Appl. No.: 13/192,006

(22) Filed: Jul. 27, 2011

(65) Prior Publication Data

US 2012/0029304 A1  Feb. 2, 2012

Related U.S. Application Data

(60) Provisional application No. 61/368,827, filed on Jul. 29, 2010.

(51) Int. Cl.
*G06F 13/00* (2006.01)
*G06F 9/44* (2006.01)

(52) U.S. Cl.
USPC .......................................... 710/303; 717/168

(58) Field of Classification Search
USPC .................... 710/303; 717/168, 169; 600/300
See application file for complete search history.

(56) References Cited

U.S. PATENT DOCUMENTS

| | | | |
|---|---|---|---|
| 5,375,604 A | 12/1994 | Kelly et al. |
| 5,491,781 A | 2/1996 | Gasperina |
| 5,724,025 A | 3/1998 | Tavori |
| 5,830,150 A | 11/1998 | Palmer et al. |
| 5,871,451 A | 2/1999 | Unger et al. |
| 5,912,656 A | 6/1999 | Tham et al. |
| 5,957,838 A | 9/1999 | Rantala |
| 6,093,146 A | 7/2000 | Filangeri |
| 6,152,754 A | 11/2000 | Gerhardt et al. |
| 6,221,012 B1 | 4/2001 | Maschke et al. |
| 6,325,540 B1 | 12/2001 | Lounsberry et al. |
| 6,352,504 B1 | 3/2002 | Ise et al. |
| 6,402,691 B1 | 6/2002 | Peddicord et al. |
| 6,544,173 B2 | 4/2003 | West et al. |
| 6,544,174 B2 | 4/2003 | West et al. |
| 6,579,231 B1 | 6/2003 | Phipps |
| 6,584,336 B1 | 6/2003 | Ali et al. |
| 6,658,276 B2 | 12/2003 | Kianl et al. |
| 6,684,090 B2 | 1/2004 | Ali et al. |
| 6,770,028 B1 | 8/2004 | Ali et al. |
| 6,792,396 B2 | 9/2004 | Inda et al. |
| 6,820,050 B2 | 11/2004 | Simmon et al. |
| 6,850,788 B2 | 2/2005 | Al-Ali |
| 6,947,780 B2 | 9/2005 | Scharf |
| 6,996,427 B2 | 2/2006 | Ali et al. |
| 7,002,468 B2 | 2/2006 | Eveland et al. |

(Continued)

FOREIGN PATENT DOCUMENTS

| | | |
|---|---|---|
| WO | WO 2005114524 | 12/2005 |
| WO | WO 2006006107 | 1/2006 |
| WO | WO 2006064397 | 6/2006 |

*Primary Examiner* — Glenn A Auve
(74) *Attorney, Agent, or Firm* — Shvarts & Leiz LLP

(57) ABSTRACT

A patient monitoring system is provided which includes a platform and one or more monitoring modules. Monitoring modules include parameter modules for monitoring physiological activity of a patient, and utility modules for providing additional functionality to the patient monitoring system. A platform and one or more monitoring modules may be coupled to form a communications bus, allowing communication between any of the plurality of coupled devices. Updates such as software upgrades may be provided by a monitoring module to a platform or other monitoring module to update functionality.

19 Claims, 7 Drawing Sheets

(56) References Cited

U.S. PATENT DOCUMENTS

| | | |
|---|---|---|
| 7,249,036 B2 | 7/2007 | Bayne |
| 7,316,648 B2 | 1/2008 | Kelly et al. |
| 7,373,193 B2 | 5/2008 | Al-Ali et al. |
| 7,383,358 B1 | 6/2008 | Kennedy |
| 7,530,949 B2 | 5/2009 | Ali et al. |
| 7,542,878 B2 | 6/2009 | Nanikashvili |
| 7,657,849 B2 | 2/2010 | Chaudhri et al. |
| 7,702,382 B2 | 4/2010 | Xue et al. |
| 8,046,721 B2 | 10/2011 | Chaudhri et al. |
| 8,266,349 B2 * | 9/2012 | Eaton et al. ............ 710/62 |
| 8,286,103 B2 | 10/2012 | Chaudhri et al. |
| 2005/0094203 A1 * | 5/2005 | Rodriguez et al. ......... 358/1.16 |
| 2006/0094936 A1 | 5/2006 | Russ |
| 2006/0098666 A1 | 5/2006 | Francis Conde Powell |
| 2006/0229503 A1 | 10/2006 | Fluegel |
| 2006/0235281 A1 | 10/2006 | Tuccillo |
| 2007/0004971 A1 | 1/2007 | Riley et al. |
| 2007/0282177 A1 | 12/2007 | Pilz |
| 2008/0045809 A1 | 2/2008 | Hermannsson |
| 2008/0081954 A1 | 4/2008 | Meyer et al. |
| 2008/0097550 A1 | 4/2008 | Dicks et al. |
| 2008/0097917 A1 | 4/2008 | Dicks et al. |
| 2008/0103554 A1 | 5/2008 | Dicks et al. |
| 2008/0114221 A1 | 5/2008 | Tso |
| 2008/0191866 A1 | 8/2008 | Falck et al. |
| 2008/0221404 A1 | 9/2008 | Tso |
| 2008/0294462 A1 | 11/2008 | Nuhaan et al. |
| 2010/0261977 A1 * | 10/2010 | Seely ............ 600/300 |
| 2011/0083141 A1 * | 4/2011 | Westberg et al. ......... 725/31 |

* cited by examiner

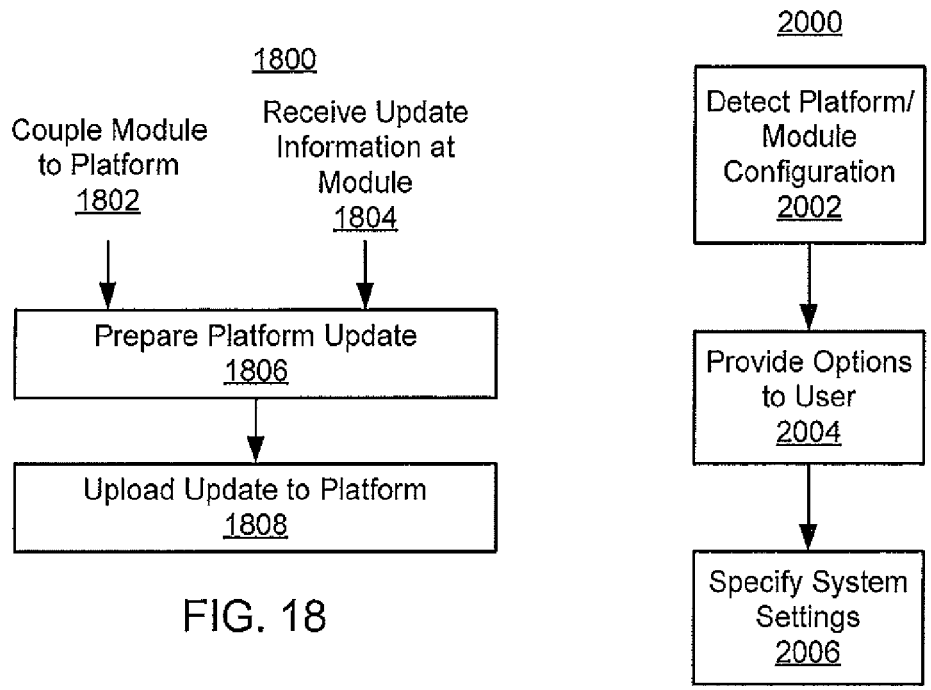
FIG. 18
FIG. 20
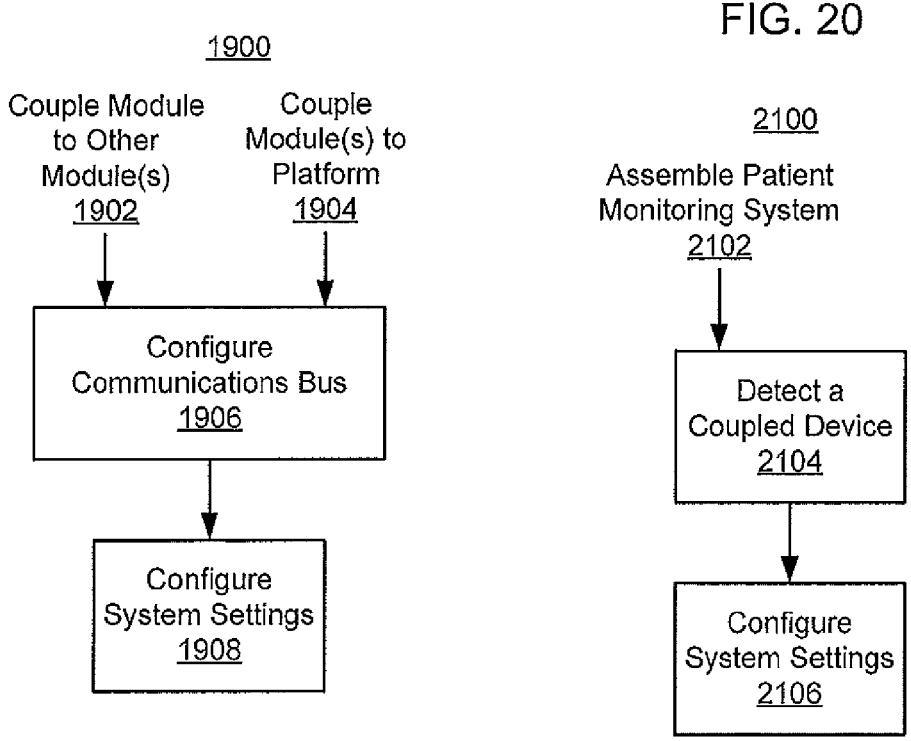
FIG. 19
FIG. 21

CONFIGURABLE PATIENT MONITORING SYSTEM

This application claims priority to U.S. Provisional Patent Application No. 61/368,827, filed on Jul. 29, 2010, entitled "Common Monitor Platform Interface and Modularity Design," which is hereby incorporated by reference herein, in its entirety.

FIELD

The present disclosure relates to configurable patient monitoring systems.

SUMMARY

A patient monitoring system is disclosed which includes a platform and at least one monitoring module. The monitoring module may be communicatively coupled to the platform forming a communication bus. The communications bus between the monitoring platform and the monitoring module allows the monitoring module to update the platform. In some embodiments, utility modules may also be coupled to the platform and monitoring module to provide additional functionality.

In some embodiments, the patient monitoring system may update the platform to allow the platform to communicate with multiple modules when the multiple modules are coupled to the platform (e.g., simultaneously coupled or otherwise). Updating the platform may include providing an application for processing an output of a monitoring module, updating software of the platform, updating preference information, updating communication instructions, updating templates of the platform, updating settings of the patient monitoring system, any other suitable update, or any combination thereof. In some embodiments, the monitoring module includes a communications interface coupled to an external device (i.e., a source), and the monitoring module receives update information from the external device. The monitoring module may be configured to update the platform at a predetermined time schedule based at least in part on the update information received form the source.

In some embodiments, a patient monitoring system may include a platform and a plurality of monitoring modules coupled in series, a terminal module of the plurality of monitoring modules being coupled to the platform to form a series communication bus between the platform and the plurality of monitoring modules. The monitoring modules may include at least one parameter module such as, for example, a pulse oximeter configured to determine blood oxygen saturation of a patient. The series communication bus may allow each of the monitoring modules to communicate with any other monitoring modules, and may allow each of the monitoring modules to communicate with the platform. The monitoring modules may also include at least one utility module such as, for example, a power supply module, a memory storage module, a signal processing module, a media player module, an audio/visual module, a user interface module, a communications module, an application module, an upgrade module, a calibration module, any other suitable module, or any combination thereof. In some embodiments, if any or all of the monitoring modules becomes uncoupled from the platform, the platform need not be configured to monitor physiological activity of a patient.

BRIEF DESCRIPTION OF THE FIGURES

The above and other features of the present disclosure, its nature and various advantages will be more apparent upon consideration of the following detailed description, taken in conjunction with the accompanying drawings in which:

FIG. 18 is a flow diagram showing illustrative steps for updating a platform, in accordance with some embodiments of the present disclosure;

FIG. 19 is a flow diagram showing illustrative steps for configuring a patient monitoring system, in accordance with some embodiments of the present disclosure;

FIG. 20 is a flow diagram showing illustrative steps for specifying system settings, in accordance with some embodiments of the present disclosure; and FIG. 21 is a flow diagram showing illustrative steps for configuring a patient monitoring system based on device detection, in accordance with some embodiments of the present disclosure.

DETAILED DESCRIPTION OF THE FIGURES

The present disclosure is directed towards module-based patient monitoring systems. A patient monitoring system may include a platform, one or more parameter modules, one or more utility modules, one or more sensors, any other suitable equipment, or any combination thereof. In some embodiments, a plurality of monitoring modules may be communicatively coupled to a platform to form a patient monitoring system. A parameter module provides physiological monitoring functionality, while a utility module provides other functionality. In some embodiments, a platform may provide a common base for coupling monitoring modules or other equipment to create patient monitoring system. In some embodiments, one or more monitoring modules may couple to other monitoring modules, and a platform may couple to at least one of the monitoring modules to create a patient monitoring system. In some embodiments, monitoring modules may provide updates such as upgrades to a patient monitoring system to expand or otherwise alter the patient monitoring system's capabilities.

Figure 1:
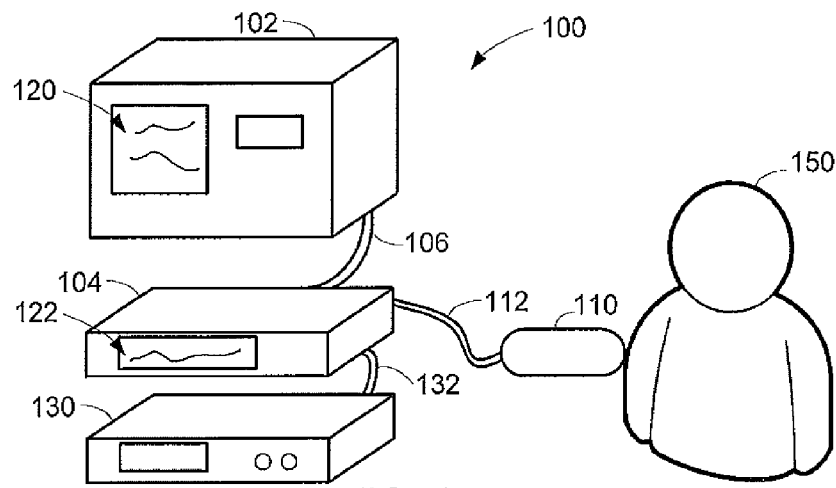
FIG. 1 shows an illustrative patient monitoring system coupled to a patient, in accordance with some embodiments of the present disclosure.

FIG. 1 shows an illustrative patient monitoring system 100. Patient monitoring system 100 may include platform 102, parameter module 104, and sensor unit 110. Patient monitoring system 100 may be used to monitor physiological information of a patient 150. Although patient monitoring system 100 is shown illustratively in FIG. 1 as having a single parameter module, any suitable number of parameter modules and utility modules, of any suitable type, may be used.

Platform 102 may include a display 120 which may be a cathode ray tube display, a flat panel display (as shown) such as a liquid crystal display (LCD) or a plasma display, or may include any other type of display now known or later developed. In some embodiments, platform 102 may be configured to provide display 120, based on information received from parameter module 104 and from other medical monitoring devices or systems (not shown). For example, platform 102 may be configured to display an estimate of a patient's blood oxygen saturation generated by parameter module 104 (referred to as an "$SpO_2$" measurement), pulse rate information from parameter module 104 and blood pressure from parameter module 104 on display 120.

Platform 102 may include any one or more user interface devices which may include, for example, a speaker, microphone, touchscreen, display (e.g., all or part of display 120), mouse, keyboard, keypad, any other suitable hardware, any suitable software applications for providing a user interface, or any combination thereof.

Parameter module 104 may be configured to calculate physiological parameters (e.g., pulse rate, blood pressure, blood oxygen saturation, respiration rate) based at least in part on data relating to information (e.g., signals) received from one or more sensor units such as sensor unit 110. In some embodiments, calculations may be performed on sensor unit 110 or an intermediate device and the result of the calculations may be passed to parameter module 104. Further, parameter module 104 may include a display 122 configured to display one or more physiological parameters (e.g., values, time series) or other information about the system. In some embodiments, parameter module 104 may include a speaker to provide an audible sound such as, for example, sounding an audible alarm in the event that a patient's physiological parameters are not within a predefined normal range.

In some embodiments, sensor unit 110 may be connected to and draw its power from parameter module 104 as shown by cable 112. In another embodiment, the sensor may be wirelessly connected to parameter module 104 and include its own battery or power supply (not shown). In some embodiments, sensor unit 110 may be communicatively coupled to parameter module 104 via a cable 112. In some embodiments, a wireless transmission device (not shown) or the like may be used instead of or in addition to cable 112.

In an illustrative example, sensor unit 110 may be a pulse oximeter sensor, and parameter module 104 may provide pulse oximeter functionality. For example, sensor unit 110 may include an emitter such as a light emitting diode (LED) for emitting light at one or more wavelengths into a patient's tissue. A detector may also be provided in sensor unit 110 for detecting the light originally from the emitter that emanates from the patient's tissue after passing through the tissue. Any suitable physical configuration of an emitter and a detector may be used. In some embodiments, sensor unit 110 may include multiple emitters and/or detectors, which may be spaced apart. For example, multiple emitters may include a Red LED and an IR LED for emitting light into the tissue of patient 150 at particular wavelengths used to calculate physiological parameters. For example, the Red wavelength may be between about 600 nm and about 700 nm, and the IR wavelength may be between about 800 nm and about 1000 nm. In embodiments where a sensor array is used in place of a single sensor, each sensor may be configured to emit a single wavelength. For example, a first sensor emits only a Red light while a second emits only an IR light. In another example, the wavelengths of light used are selected based on the specific location of the sensor.

Patient monitoring system 100 may include one or more additional sensor units (not shown) which may be coupled to parameter module 104, or additional parameter modules (not shown). An additional sensor unit may be the same type of sensor unit as sensor unit 110, or a different sensor unit type than sensor unit 110. Multiple sensor units may be capable of being positioned at two different locations on a subject's body; for example, a first sensor unit may be positioned on a patient's forehead, while a second sensor unit may be positioned at a patient's fingertip (e.g., for determining blood pressure of patient 150).

Sensor unit 110 may each detect any signal that carries information about a patient's physiological state, such as an electrocardiograph signal, arterial line measurements, or the pulsatile force exerted on the walls of an artery using, for example, oscillometric methods with a piezoelectric transducer. For example, sensor unit 110 may include one or more electrodes for monitoring electroencephalographic activity, electromyographic activity, electrocardiographic activity, or other electrical activity of patient 150.

In some embodiments, patient monitoring system 100 may include a plurality of sensors forming a sensor array in lieu of either or both of the sensor units. For example, each of the sensors of a sensor array may be a complementary metal oxide semiconductor (CMOS) sensor. Alternatively, each sensor of an array may be charged coupled device (CCD) sensor. In an embodiment, a sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier. It will be understood that any type of sensor, including any type of physiological sensor, may be used in one or more sensor units in accordance with the systems and techniques disclosed herein. It is understood that any number of sensors measuring any number of physiological signals may be used to determine physiological information in accordance with the techniques described herein.

In some embodiments, sensor unit 110 may include an encoder or other identification information which may include information about sensor unit 110, such as what type of sensor it is (e.g., whether the sensor is intended for placement on a forehead or digit), the wavelengths of light emitted by an emitter, a number of electrodes, any other type of suitable information, or any combination thereof. This information may be used by parameter module 104 to select appropriate algorithms, lookup tables and/or calibration coefficients stored in monitor 104 for calculating the patient's physiological parameters. An encoder may contain information specific to patient 150, such as, for example, the patient's age, weight, and diagnosis. This information about a patient's characteristics may allow parameter module 104 to determine, for example, patient-specific threshold ranges in which the patient's physiological parameter measurements should fall and to enable or disable additional physiological parameter algorithms. This information may also be used to select and provide coefficients for equations from which, for example, blood pressure and other measurements may be determined based at least in part on the signal or signals received at sensor unit 110. For example, some pulse oximetry sensors rely on equations to relate an area under a portion of a photoplethysmograph (PPG) signal corresponding to a physiological pulse to determine blood pressure. These equations may contain coefficients that depend upon a patient's physiological characteristics as stored in an encoder. An encoder may, for instance, be a coded resistor which stores values corresponding to the type of sensor unit 110 or the type of each sensor in the sensor array, the wavelengths of light emitted by an emitter on each sensor of the sensor array, and/or the patient's characteristics. In some embodiments, an encoder may include a memory on which information may be stored for communication to parameter module 104.

Parameter module 104 may be communicatively coupled to platform 102 via a cable 106 that is coupled to respective communications ports of parameter module 104 and platform 102. In some embodiments, parameter module 104 and platform 102 may communicate with one another wirelessly (not shown). In some embodiments, parameter module 104, platform 102, or both may be coupled to a network to enable the sharing of information with servers or other workstations (not shown). Parameter module 104 may be powered by a battery (not shown) or by a conventional power source such as a wall outlet (not shown).

In some embodiments, patient monitoring system 100 may include a utility module 130. Any suitable number and type of utility modules may be included in patient monitoring system 100. In some embodiments, patient monitoring system 100 need not include any utility module. Utility modules are monitoring modules configured to provide functions other than physiological monitoring such as providing, for example, power, memory capacity, signal processing capabilities, media playback functions, audio/visual functions, user interface functions, communications interfaces and functions, applications, upgrade capabilities, calibration functions, processing capabilities, storage/reservoir capacity, database capabilities, patient interface capabilities, alarm capabilities, any other suitable functions, capacities or capabilities, or any combination thereof. The discussion of FIG. 3 herein includes more details regarding the various monitoring modules. Utility module 130 may communicatively couple to parameter module 104, platform 102, or both via coupling 132 which may be a wired or wireless communication coupling.

In some embodiments, platform 102 may include a common bus to which a parameter module (e.g., parameter module 104) and a utility module (e.g., utility module 130) couple. The common bus may allow monitoring modules to be "daisy-chained" (i.e., connected in series with a terminal module coupled to the platform) to one another, or directly coupled to respective communications ports of platform 102. In some embodiments, monitoring modules may be connected in a branching network, in which a monitoring module may be communicatively coupled to two or more other devices.

In some embodiments, a monitoring module may be a standalone device. In some embodiments, a monitoring module need not be a standalone device, and may require coupling to a platform to allow physiological monitoring. Likewise, a platform may be, but need not be, a standalone device. In some embodiments, for example, a platform may require that at least one monitoring module is coupled to the platform to allow physiological monitoring.

The modular system shown in FIG. 1 may provide several characteristics which may be desired such as ability to scale as needed, ability of a user to only purchase desired monitoring modules, clarity in the function of a particular monitoring module which may be configured for performing particular functions, standardization in manufacturing of monitoring modules, versatility in the capability of a patient monitoring system, and other characteristics which may be provided.

Although sensor unit 110 is shown illustratively in FIG. 1 as being coupled to parameter module 104, it need not be. For example, in some embodiments, sensor unit 110 may be coupled to platform 102 rather than parameter module 104. In some embodiments, parameter module 104 may receive a raw or processed (e.g., amplified, filtered, offset, sampled, digitized) physiological signal of sensor unit 110 from platform 102.

Figure 2:
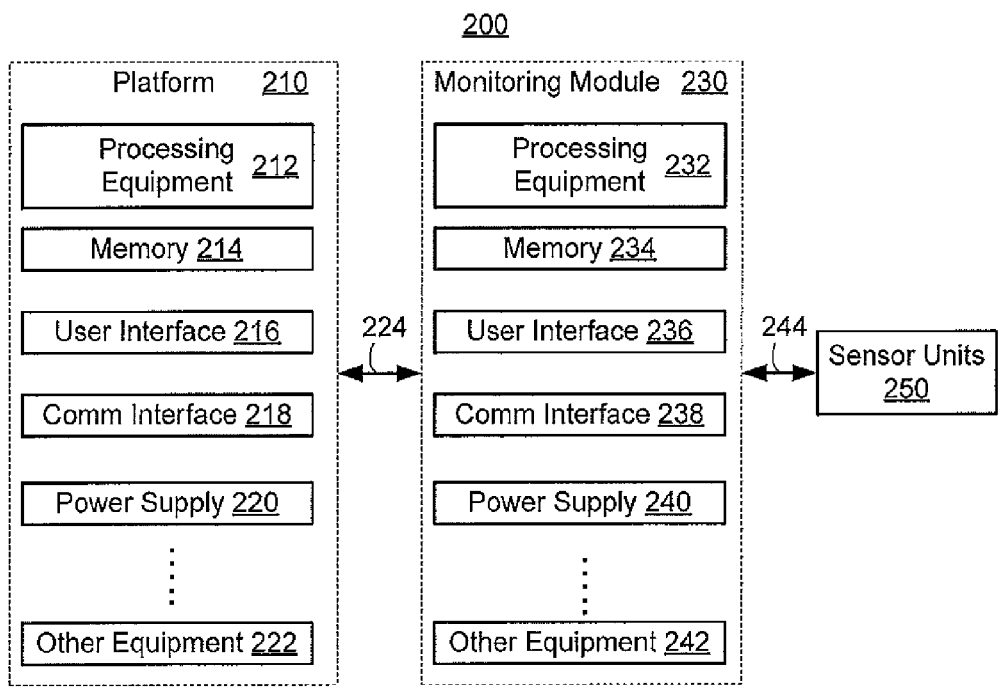
FIG. 2 is a block diagram of an illustrative patient monitoring system including a platform, monitoring module and sensor, in accordance with some embodiments of the present disclosure.

FIG. 2 is a block diagram of an illustrative patient monitoring system 200 including a platform 210, monitoring module 230 and sensor units 250, in accordance with some embodiments of the present disclosure.

Monitoring module 230 may include processing equipment 232, memory 234 (e.g., random access memory (RAM), read-only memory (ROM), cache), user interface 236, communications interface 238, power supply 240, any other suitable equipment 242 connected to one or more internal buses, or any combination thereof. In some embodiments, other equipment 242 may include a chassis to structurally maintain the components of monitoring module 230.

Processing equipment 232 may be adapted to execute software, which may include an operating system and one or more applications, as part of performing the functions described herein. Processing equipment 232 may include a microprocessor, a parallel processor arrangement, a central processing unit, any other suitable processors in any suitable processing arrangement, or any combination thereof. In some embodiments, processing equipment 232 may be configured to process electrical signals received from sensor units 250 (which may include one or more sensors) via coupling 244. For example, processing equipment 232 may be configured to convert (e.g., a current to voltage conversion, an analog to digital conversion), amplify, filter (e.g., low pass filter, notch filter, band filter), sample, store (e.g., in queue), buffer, decimate, multiplex/de-multiplex, modulate/demodulate, perform any other signal processing function on a signal received from sensor units 250, or any combination thereof. Processing equipment 232 may be configured to calculate one or more physiological parameters based at least in part on information received from sensor units 250. For example, processing equipment 232 may calculate physiological parameter values (e.g., a time series), signal metrics (e.g., a time series), changes or rates of change of parameters or metrics, trends (e.g., values increasing, decreasing, or accelerating), deviations from a limit, any other suitable quantity or qualitative measure, or any combination thereof.

In some embodiments, processing equipment 232 may include a time processing unit (TPU) which may provide timing control signals. For example, a TPU may include a clock, counter or other timing function to coordinate communication (e.g., with platform 210, sensor units 250, other monitoring module, network, an external device, or combinations thereof), activity of sensor units 250, updating of a display, recording of data, any other function which may be timed or scheduled, or any combination thereof. For example, a TPU may be used to control light drive circuitry (e.g., included in other equipment 242), which may control when a Red LED and an IR LED of sensor units 250 are alternately illuminated, and multiplex such time modulated signals. A TPU may also control the gating-in of signals from a detector (e.g., a photodetector, an electrode) of sensor units 250, such as through an amplifier and switching circuit. The TPU may ensure signals are sampled at the proper time (e.g., depending upon which light source is illuminated for a two wavelength time-modulated pulse oximeter). The received signal from a detector of sensor units 250 may be passed through an amplifier, low pass filter, and analog-to-digital converter of processing equipment 232. The digital data may then be stored in a queued serial module (QSM) (or buffer) for later downloading to memory 234 as the QSM fills. In some embodiment, there may be multiple separate parallel paths having equivalent components to process multiple received signals from sensor units 250.

In some embodiments sensor units 250 may include an encoder and may communicate encoded information relating to patient characteristics to monitoring module 230. Processing equipment 232 may include a decoder may translate these signals to enable the processor to, for example, determine the thresholds based at least in part on algorithms or look-up tables stored in memory 234. In some embodiments, user interface 236 may be used enter information, select one or more options, provide a response, input settings, any other suitable inputting function, or any combination thereof. User interface 236 may be used to enter information about the patient, such as age, weight, height, diagnosis, medications, treatments, and so forth. In some embodiments, a display of user interface 236 may exhibit a list of values which may generally apply to the patient, such as, for example, age ranges or medication families, which the user may select using user interface 236.

Memory 234 may include suitable computer-readable media which may be used in the system for data storage. Computer-readable media are capable of storing information that can be interpreted by processing equipment 232. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

User interface 236 may include any suitable hardware, software, or both, which may allow a user to interact with monitoring module 230. User interface 236 may include a speaker, microphone, touchscreen, display, mouse, keyboard, keypad, any other suitable hardware, any suitable software applications for providing a user interface, or any combination thereof. For example, in some embodiments, user interface 236 may include software for displaying a plurality of options on a display, and may allow a user to select any of the plurality of options using hard commands of a keypad. Any suitable user interface may be coupled to, or included as a part of, monitoring module 230. In some embodiments, user interface 236 provides the interface between patient monitoring system 200, monitoring module 230, or both, and the user.

Communications ("Comm") interface 238 may include any suitable hardware, software, or both, which may allow monitoring module 230 to communicate with electronic circuitry, a device, or a network, or any combinations thereof. Communications interface 238 may include one or more receivers, transmitters, transceivers, antennas, plug-in connectors, ports, communications buses, communications protocols, device identification protocols, any other suitable hardware or software, or any combination thereof. Communications interface 238 may be configured to allow wired communication (e.g., using USB, RS-232 or other standards), wireless communication (e.g., using WiFi, IR, WiMax, BLUETOOTH, UWB, or other standards), or both. For example, communications interface 238 may be configured using a universal serial bus (USB) protocol (e.g., USB 2.0, USB 3.0), and may be configured to couple to other devices (e.g., platform 210, sensor units 250) using a four-pin USB standard Type-A connector (e.g., plug and/or socket) and cable. In a further example, communications interface 238 may include an inter-integrated circuit (I2C) bus which may include a serial data line (SDL) and a serial clock (SCL). In a further example, communications interface 238 may include a universal asynchronous receiver/transmitter (UART) to provide serial communications. In a further example, communications interface 238 may include a plug-in connector, with pins allocated for digital data transfer, power transfer (e.g., external power supply, charging), timing signals (e.g., a clock), and any other suitable functions. Communications interface 238 may send and receive information using couplings 244 and 224, which may be any suitable type of electrical, optical, wireless, or other suitable communicative coupling, or any combination thereof. In some embodiments, coupling 244 may include a multi-pin electrical connection interface, such as that disclosed in U.S. patent application Ser. No. 13/149,688 filed May 31, 2011, titled "PATIENT MONITORING PLATFORM INTERFACE," which is hereby incorporated by reference herein in its entirety. In some embodiments, communications interface 238 may include an internal bus such as, for example, one or more slots for insertion of expansion cards (e.g., expansion printed circuit boards).

In an illustrative example, coupling 224 may include a multi-pin connector interface including pins for data transmission (e.g., UART communications, SDA communications, USB communications), clock signals, power transfer (e.g., for supplying and receiving electrical power), diagnostic signals (e.g., insufficient power, disconnect in coupling 224), any other suitable signals, or any combination thereof. For example, physiological signals, physiological parameter values, signal metrics, any other suitable signals, or combinations thereof may be transmitted using pins configured for UART communications. In a further example, timing signals may be transmitted over pins configured for SCL functionality (e.g., for coordinating communications among multiple devices such as platforms and monitoring modules). In a further example, a platform may reset a monitoring module by transmitting suitable signals using pins configured for SCL and SDA communications.

Power supply 240 may include batteries (e.g., primary or secondary), photovoltaic cells, a transformer for transforming 120 VAC power from a municipal grid, any suitable power cables, any suitable power conditioning/managing circuitry (e.g., rectifiers, inverters, amplifiers, transformers, voltage regulators, fuses, breakers, switches), or any combination thereof. In some embodiments, monitoring module 230 need not include power supply 240, and may be powered by platform 210 via coupling 224 (e.g., via suitable leads of a USB coupling).

Monitoring module 230 may include other equipment 242 which may include, for example, media players, structural components, indicators, or any other suitable equipment not specified above.

Platform 210 may include processing equipment 212, memory 214 (e.g., random access memory (RAM), read-only memory (ROM), cache), user interface 216, communications interface 218, power supply 220, any other suitable equipment 222 connected to one or more internal buses, or any combination thereof. In some embodiments, other equipment 222 may include a chassis to structurally maintain the components of platform 210.

Processing equipment 212 may be adapted to execute software, which may include an operating system and one or more applications, as part of performing the functions described herein. Processing equipment 212 may include a microprocessor, a parallel processor arrangement, a central processing unit, any other suitable processor in any suitable processing arrangement, or any combination thereof. Processing equipment 232 may be configured to calculate, or receive from monitoring module 230, one or more physiological parameter values based at least in part on information received by monitoring module 230 from sensor units 250. For example, processing equipment 212 may receive physiological parameter values (e.g., a calculated time series), signal metrics (e.g., a calculated time series), changes or rates of change of parameters or metrics, trends (e.g., values increasing, decreasing, or accelerating), deviations from a limit, any other suitable quantity or qualitative measure, or any combination thereof from monitoring module 230, and platform 210 may display any or all of this information on a display of user interface 216.

In some embodiments, processing equipment 212 may include a time processing unit (TPU) which may provide timing control signals. For example, a TPU may include a clock, counter or other timing function to coordinate communication with monitoring module 230, sensor units 250, other monitoring module, network, an external device, or combinations thereof. For example, digital data may be received from monitoring module 230 and may then be stored in a queued serial module (QSM) or buffer for later downloading to memory 214 as the QSM fills. In some embodiment, there may be multiple separate parallel paths having equivalent components to process multiple received signals from monitoring module 230.

In some embodiments, platform 210 may store, communicate, or both, information relating to patient characteristics to monitoring module 230. In some embodiments, user interface 216 may be used enter information, select one or more options, provide a response, input settings, any other suitable inputting function, or any combination thereof. User interface 216 may be used to enter information about the patient, such as age, weight, height, diagnosis, medications, treatments, and so forth. In some embodiments, a display of user interface 236 may exhibit a list of values which may generally apply to the patient, such as, for example, age ranges or medication families, which the user may select using user interface 216.

Memory 214 may include suitable computer-readable media which may be used in the system for data storage. Computer-readable media are capable of storing information that can be interpreted by processing equipment 212. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

User interface 216 may include any suitable hardware, software, or both, which may allow a user to interact with platform 210. User interface 216 may include a speaker, microphone, touchscreen, display, mouse, keyboard, keypad, any other suitable hardware, any suitable software applications for providing a user interface, or any combination thereof. For example, in some embodiments, user interface 216 may include software for displaying a time series of a physiological parameter on a display, and may allow a user to configure the display using soft commands of a touchscreen. Any suitable user interface may be coupled to, or included as a part of, platform 210.

Communications ("Comm") interface 218 may include any suitable hardware, software, or both, which may allow platform 210 to communicate with electronic circuitry, a device, or a network, or any combinations thereof. Communications interface 218 may include one or more receivers, transmitters, transceivers, antennas, plug-in connectors, ports, communications buses, communications protocols, device identification protocols, any other suitable hardware or software, or any combination thereof. Communications interface 218 may be configured to allow wired communication (e.g., using USB, RS-232 or other standards), wireless communication (e.g., using WiFi, IR, WiMax, BLUETOOTH, UWB, or other standards), or both. For example, communications interface 218 may be configured using a USB protocol (e.g., USB 2.0, USB 3.0), and may be configured to couple to other devices (e.g., monitoring module 230, other modules, other platforms) using a four-pin USB standard Type-A connector (e.g., plug and/or socket) and cable. In a further example, communications interface 218 may include an I2C bus which may include a SDL and a SCL. In a further example, communications interface 218 may include a UART to provide serial communications. In a further example, communications interface 218 may include a plug-in connector, with pins allocated for digital data transfer, power transfer (e.g., external power supply, charging), timing signals (e.g., a clock), and any other suitable functions. In some embodiments, communications interface 218 may include an internal bus such as, for example, one or more slots for insertion of expansion cards (e.g., monitoring modules configured as PCBs).

Power supply 220 may include batteries (e.g., primary or secondary), photovoltaic cells, a transformer for transforming 120 VAC power from a municipal grid, any suitable power cables, any suitable power conditioning/managing circuitry (e.g., rectifiers, inverters, amplifiers, transformers, voltage regulators, fuses, breakers, switches), or any combination thereof. In some embodiments, platform 210 may provide power to monitoring module 230 via coupling 224 (e.g., via suitable leads of a USB coupling, via a coaxial cable).

Platform 210 may include other equipment 222 which may include, for example, media players, structural components, indicators, or any other suitable equipment not specified above.

In some embodiments, components of platform 210 and monitoring module 230 may function in concert. For example, user interface 216 of platform 210 may provide user inputted signals to monitoring module 230 via communication between communication interfaces 218 and 238. In some embodiments, monitoring module 230 need not include user interface 236, because user interaction may be provided by user interface 216. In a further example, monitoring module 230 may manage power from power supply 220 of platform 210 to power sensor units 250, and accordingly monitoring module 230 need not include power supply 240. In a further example, processing equipment 232 may include hardware, software, or both, for signal processing, but calculation of physiological parameters may be performed by processing equipment 212 of platform 210. In a further example, processing equipment 232 may include hardware, software, or both, for signal processing and calculation of physiological parameters, and physiological information (e.g., physiological parameter values) may be communicated to platform 210, which need not be configured to calculate physiological parameters. Any suitable interaction of the components of platform 210, monitoring module 230, and sensor units 250 may be used to monitor physiological activity of a patient. Accordingly, platform 210 and monitoring module 230 need not include all of the respective components shown in FIG. 2. Also accordingly, sensor units 250 may include any suitable components of platform 210, monitoring module 230, or both.

Although not shown in FIG. 2, in some embodiments, platform 210 may be configured to receive physiological signals directly (i.e., not via monitoring module 230) from sensor units 250. For example, communications interface 218 may include any of the functionality and components of communications interface 238 for communicating with sensor units 250. In some embodiments, physiological signals communicated to platform 210 from sensor units 250 may be subsequently transmitted to monitoring module 230 for processing (e.g., signal processing, calculating physiological parameters).

Figure 3:
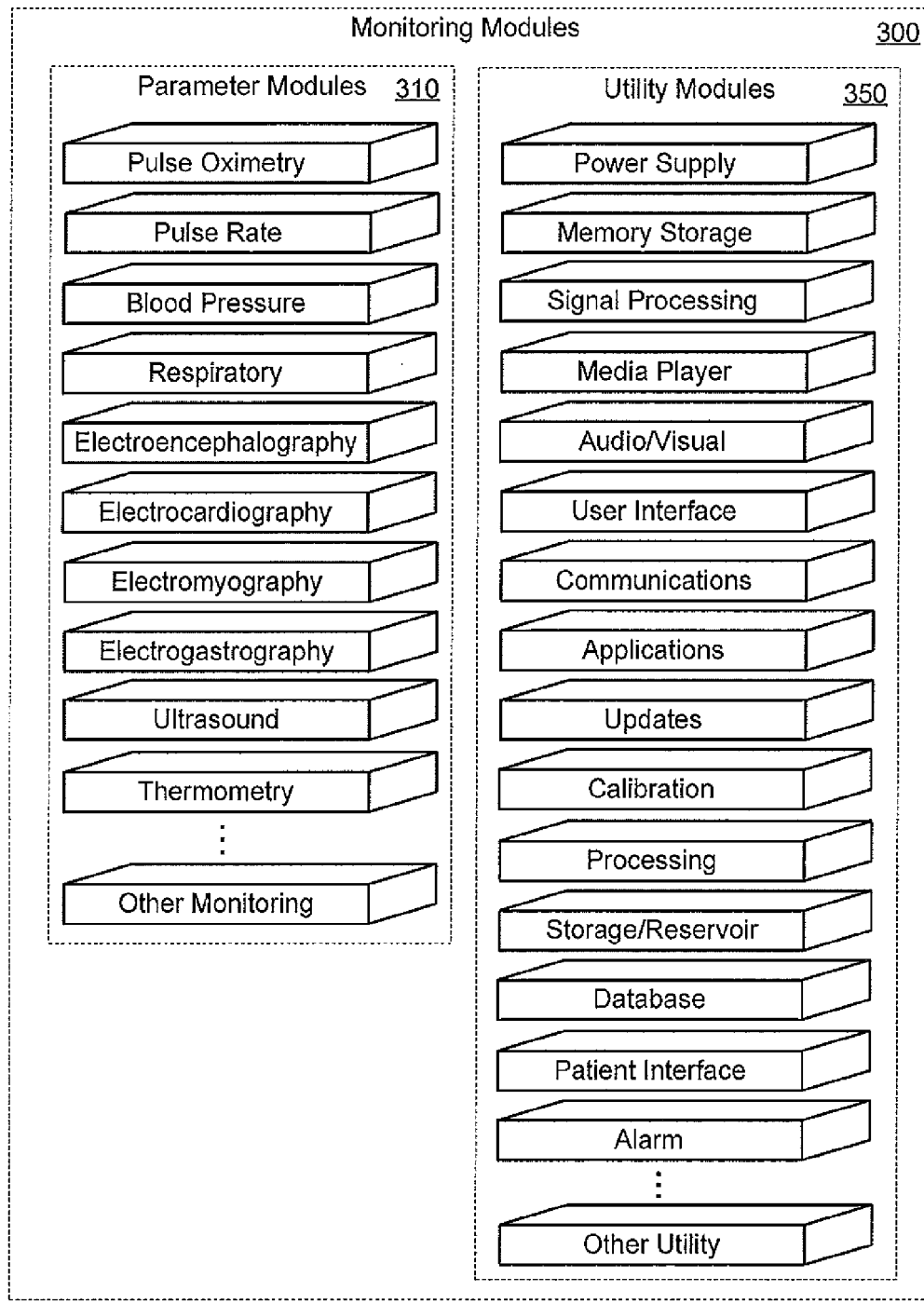
FIG. 3 shows a variety of illustrative parameter and utility module types, in accordance with some embodiments of the present disclosure.

FIG. 3 shows a variety of illustrative monitoring and utility module types, in accordance with some embodiments of the present disclosure. Monitoring modules 300 may include a variety of module types, each with particular capabilities and functionalities. Monitoring modules 300 may include parameter modules 310 and utility modules 350.

Parameter modules 310 include modules configured to monitor physiological activity of a patient. Parameter modules 310 include monitoring modules configured to provide pulse oximetric information, pulse rate information, blood pressure information, respiratory information (e.g., respiration rate, inspiration volume), electroencephalographic (EEG) information, electrocardiographic (ECG) information, electromyographic (EMG) information, electrogastrographic (EGG) information, ultrasound information, thermometry information, any suitable information regarding any other physiological activity, or any combination thereof.

Parameter modules may be coupled to suitable sensor units to receive physiological signals in connection with a patient. Parameter modules may be configured to control one or more sensor units, provide power to one or more sensor units, receive signals from one or more sensor units, perform any other suitable interaction with one or more sensor units, or any combination thereof. For example, a pulse oximetry parameter module may be connected to one or more sensor units including an emitter and a detector for determining blood oxygen saturation. In a further example, an EEG parameter module may be connected to one or more sensor units including an array of electrodes for determining a patient's brain wave activity. In some embodiments, a parameter module may be configured to calculate more than one physiological parameter. For example, a pulse oximetry parameter module may be configured to calculate blood oxygen saturation, pulse rate, and respiration rate. In a further example, an EEG parameter module may be configured to calculate both EEG parameters and EMG parameters by evaluating particular spectral ranges of electrical signals received from one or more electrodes in contact with a patient. Any suitable physiological information, or combinations thereof, may be monitored by a parameter module.

Utility modules 350 include monitoring modules configured to provide any other suitable function except for physiological monitoring. Utility modules 350 include monitoring modules configured to provide power, memory, signal processing capabilities, media playing capabilities (e.g., a DVD player), audio/visual capabilities (e.g., video decoding), user interfacing capabilities (e.g., a touchscreen), communications capabilities (e.g., providing a wireless interface such as WiFi), application capabilities (e.g., software programs allowing further data processing or visualization), updates (e.g., software upgrades), calibration services (e.g., checking calibration of a sensor unit), processing capacity, storage or reservoir capacity, database capacity, patient interface capabilities, alarm capabilities, any other suitable utility, or any combination thereof.

Power supply modules may include one or more batteries, transformers (e.g., AC-DC transformers), charge indicators, photovoltaic cells, any other suitable components for supplying or conditioning electrical power, or any combination thereof. In some embodiments, inclusion of a power supply module in a patient monitoring system may extend the operating life of the system in situations where grid power is not desired (e.g., portable applications) or unavailable (e.g., remote locations).

Memory storage modules may include RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store information. In some embodiments, a memory storage module need not include substantial memory, but may accept or otherwise communicate with external memory devices such as portable flash USB drives. For example, a memory storage module may include one or more USB standard four pin Type A ports for accepting a USB flash drive form a user. In a further example, a memory storage module may include a magnetic disk hard drive.

Signal processing modules may include current to voltage (I-V) converters, amplifiers, filters (e.g., Bessel filters), analog to digital converters, samples, decimators, multiplexers/de-multiplexers, modulators/de-modulators, shields (e.g., to reduce interference), summers, any other suitable components for processing received signals (e.g., physiological signals), or any combination thereof. In some embodiments, a sensor unit may be coupled to a signal processing module, which may in turn be coupled to a parameter module which may receive processed sensor signals from the signal processing module. In some embodiments, the functionality of signal processing module may be included in a parameter module.

Media player modules may include devices which read, write, or both, CDs, DVDs, floppy disks, zip disks, cassettes, SecureDigital (SD) cards, MultiMediaCard (MMC), subscriber identity module (SIM) cards, any other suitable media, or any combination thereof. In some embodiments, a media player module may be configured to receive media files and play, convert, record, or otherwise manage the media files using software. In some embodiments, the functionality of media player module may be included in a parameter module.

Audio/visual (AV) modules may include any suitable software, hardware, or both, which may provide audio or video support to a platform. An A/V module may include a speaker, a display, a media player, a video decoder, a video codec, graphics drivers, any other suitable A/V components or software, or any combination thereof. In some embodiments, an A/V module may include one or more ports configured to couple to video cables (e.g., VGA connectors and cables, S-video connectors and cables, DVI connectors and cables, composite video connectors and cables). In some embodiments, an A/V module may include one or more ports configured to couple to audio cables (e.g., RCA connectors and cable, TRS connectors and cable). In some embodiments, an A/V module may include one or more ports configured to couple to video/audio cables (e.g., HDMI connectors and cable, multi-ring TRS connectors and cable, IEEE 1394 standard "Firewire"). In some embodiments, the functionality of an A/V module may be included in a parameter module.

User interface modules may include a speaker, microphone, touchscreen, display, mouse, keyboard, keypad, barcode readers, camera, scanner, any other suitable hardware, any suitable software applications for providing a user interface, or any combination thereof. For example, a user interface may include a keyboard and mouse with which a user may type text, enter commands using hard buttons, manipulate a movable cursor on a display to highlight regions or select options, and otherwise provide input and/or responses to a patient monitoring system. In some embodiments, the functionality of a user interface module may be included in a parameter module (as shown in FIG. 2).

Communications modules may include any suitable hardware, software, or both, which may allow the monitoring module to communicate with other monitoring modules, platforms, network servers, devices, any other suitable devices, or any combination thereof. A communications module may include one or more receivers, transmitters, transceivers, antennas, plug-in connectors, ports, communications buses, communications protocols, device identification protocols, any other suitable hardware or software, or any combination thereof. A communications module may be configured to allow wired communication (e.g., using USB, RS-232, IEEE 802.3 ethernet or other standards), wireless communication (e.g., using WiFi, IR, WiMax, BLUETOOTH, UWB, or other standards), or both with external devices (e.g., parameter modules, network servers). For example, a communications module may be configured to communicate using the WiFi standard (i.e., IEEE 802.11), and impart WiFi capability to a patient monitoring system. In a further example, a communications module may include a modem for accessing the internet or other network via a local area network (LAN) using an Ethernet connection. In some embodiments, for example, a communication module may be a server coupled to a suitable network. In some embodiments, a communications module may be configured to communicate with a mobile user device (e.g., mobile phone, personal media player, personal digital assistant) using a telecommunications standard such as 3G or 4G mobile standards. In some embodiments, a communications module may be configured to communicate with a remote monitoring device (e.g., handheld physiological monitor) using a wireless standard such as WiFi. In some embodiments, a communications module may include an internal bus such as, for example, one or more slots for insertion of expansion cards. In some embodiments, the functionality of a communications module may be included in a parameter module.

Applications modules may include any suitable software, hardware, or both, which may provide applications or applications support to a platform. An applications module may include processing equipment, memory, a user interface, a communications interface, and/or any other suitable components to run software applications locally, access remote applications (e.g., from a remote applications server), provide any other suitable application services, or any combination thereof. For example, an application module may provide a visualization application (e.g., with plotting options for data), data management application (e.g., formatting and storing data files), report generating application, patient tracking application (e.g., appending a patient history, recalling a patient history), user tracking application, any other suitable application, or any combination thereof. In some embodiments, an application module may provide increased functionality to a patient monitoring system by providing additional software which may be used with existing hardware a patient monitoring system (e.g., for computing additional physiological parameters). For example, a patient monitoring system may be configured as a pulse oximeter (e.g., include a platform and a pulse oximetry parameter module). Addition of an applications module may provide increased graphing or data formatting capability relative to the capabilities of the existing pulse oximetry parameter module and platform. In some embodiments, an applications module may be configured to calculate physiological parameters, signal metrics, or perform other calculations not otherwise performed by a patient monitoring system without the applications module coupled. In some embodiments, the functionality of an applications module may be included in a parameter module.

Update modules may include any suitable software, hardware, or both, which may provide upgrades or other updated information to a platform, monitoring module, sensor, or combinations thereof. An update module may include processing equipment, memory, a communications interface, and/or any other suitable components to run software applications locally, access remote applications (e.g., from a remote applications server), access remote devices (e.g., a remote database server, an internet server). In some embodiments, an update module may receive update information from a source such as a manufacturer's website or server, another user, third party vendor, any other suitable information source, or combinations thereof. In some, embodiments, an update module may be preprogrammed with an update and need not access an external source. An update module may provide update information in whole, part, in redacted form, reformatted, or in otherwise processed form to a platform, monitoring module, sensor, or combinations thereof. In some embodiments, an update module may provide update information on a regular schedule. In some embodiments, an update module may provide update information at the request of a user (e.g., manual request for update), a platform, a monitoring module, a sensor, any other suitable device (e.g., which may provide an "automatic" request), any other suitable entity, or any combination thereof. An update module may provide templates, drivers, software upgrades, instructions, any other suitable information, or any combination thereof. In some embodiments, the functionality of an update module may be included in a parameter module. In some embodiments, a platform may update one or more coupled monitoring modules, using any of the functionality of an updates module.

Calibration modules may include any suitable software, hardware, or both, which may provide device or algorithm calibration or characterization. In some embodiments, a calibration module may include a reference device against which a sensor unit may be calibrated, checked for integrity, or otherwise compared. For example, a calibration module may include a reference attenuator which may allow a pulse oximetry sensor (e.g., an emitter and photodetector) to be calibrated. In a further example, a calibration module may include a sphygmomanometer to be used as a blood pressure calibration for a photoplethysmographic blood pressure parameter module and sensor.

Processing modules may include any suitable software, hardware, or both, which may provide processing capacity. A processing module may include a processor (e.g., a microprocessor), memory (e.g., RAM, ROM, cache), an internal bus, any other suitable components, or any combination thereof. In some embodiments, a processing module may augment or otherwise increase the processing capacity of a patient monitoring system (e.g., by reducing computation time per computation, or increasing the number of computations performed per second). For example, a processing module may include one or more processors which may function along with a processor of a platform as "parallel processors" under suitable control (e.g., provided by the processing module, the platform, or by a separate suitable applications module). In some embodiments, a processing module may be configured to calculate physiological parameters, signal metrics, or perform other calculations not otherwise performed by a patient monitoring system without the processing module coupled. For example, a processing module may receive photoplethysmograph (PPG) waveforms from a pulse oximeter module which may not be configured to calculate respiration rate, and the processing module may calculation respiration rate based on spectral analysis of the waveforms.

Storage/reservoir modules may include drawers, bins, shelves, tanks, vessels, catch-basin, any other suitable receptacles for solids, liquid or gases, or any combination thereof. Storage/reservoir modules may be used to store tools (e.g., wire strippers, screwdrivers, or other tools), store accessories, store first aid supplies, store electrical supplies (e.g., twist-on wire connectors, zip-ties, crimp terminals, or other electrical supplies) store spare components, hold active monitoring modules, store liquids or gases (e.g., in which case the monitoring module may be impermeable and/or leak-proof).

Database modules may include any suitable software, hardware, or both, which may provide database capacity and/or functionality. A database module may accept data entry (e.g., patient information, user information, system information), catalogue or index data (e.g., physiological data), store data (e.g., population sample data of one or more physiological parameters), perform any other suitable data management function, or any combination thereof. In some embodiments, the functionality of a database module may be included in a parameter module.

Patient interface modules may include any suitable software, hardware, or both, which may allow a patient to interact with a patient monitoring system. A patient interface module may include a biometric scanner or recognition interface (e.g., fingerprint detector, retina scanner), voice recognition software and hardware, patient input interface (e.g., a keypad or touchscreen allowing a patient to enter information, select options, or respond to queries), any other suitable interface for interacting with a patient, or any combination thereof. In some embodiments, a patient interface may store patient information, allow a patient or user to update patient information, provide current or historical patient physiological information, perform any other suitable patient interfacing function, or any combination thereof. In some embodiments, a patient interface module may be configured to read a patient identification card (e.g., an imprinted barcode) to gather information about the patient. In some embodiments, the functionality of patient interface module may be included in a parameter module.

Alarm modules may include any suitable software, hardware, or both, which may provide alarm, warning, or indication functionality to a patient monitoring system. An alarm module may include a speaker (e.g., for producing audible alerts), a buzzer, a lamp or bulb (e.g., a flashing LED to indicate a warning), processor and memory for storing alarm event notifications, any other suitable components, or any combination thereof. In some embodiments, an alarm module may include processing equipment, memory, and a communications interface, configured to receive physiological information and compare the physiological information to alarm limits in order to determine whether an alarm should be activated. In some embodiments, determination as to whether to activate an alarm may be made in another monitoring module (e.g., a parameter module, a processing module, an applications module), and the other monitoring module may communicate to the alarm module that an alarm should be activated. For example, a pulse oximetry module may determine that a patient's blood oxygen saturation is below an alarm threshold, and the pulse oximetry module may communicate to the alarm module that an alarm is to be activated. The alarm module may, in response to the pulse oximetry module's communication, provide an audible beep to alert a user and/or patient. In some embodiments, the functionality of an alarm module may be included in a parameter module.

In some embodiments, the functionality of one or more monitoring modules may be combined in a single module. For example, a pulse oximetry parameter module may also provide ROM storage capacity for storing waveforms or time series values. In a further example, a media player module may provide the ability to read/write DVDs as well as one or more USB 2.0 ports to accept flash memory drives. In a further example, an A/V module may also have media playing capabilities. Any of the functions of any monitoring or utility module may be combined with functions of any other parameter or utility module in a single monitoring module.

In an illustrative example, a platform may be initially configured to display blood oxygen saturation as calculated by a particular pulse oximeter module. A parameter module which provides pulse oximeter functionality and calculates blood oxygen saturation, pulse rate, and respiration rate may be coupled to the platform. The parameter module may include updates (e.g., updates module functionality) such as software upgrades which allow the platform to display blood oxygen saturation, pulse rate, and respiration rate.

In a further illustrative example, a platform may receive updates from an updates module, including updated algorithms for calculating blood oxygen saturation, pulse rate, and respiration rate. The platform may provide the updated algorithms to the parameter module (i.e., "update" the parameter module) to allow the parameter module to calculate blood oxygen saturation, pulse rate, and respiration rate.

Figure 4:
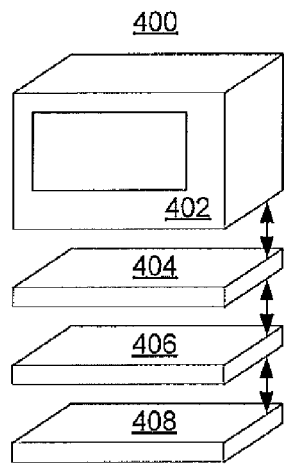
FIG. 4 shows an illustrative serial arrangement of a platform and monitoring modules, in accordance with some embodiments of the present disclosure.

FIG. 4 shows an illustrative serial arrangement 400 of a platform 402 and monitoring modules 404, 406, and 408, in accordance with some embodiments of the present disclosure. Arrangement 400 is a "daisy-chain" series arrangement because platform 402 and monitoring modules 404, 406, and 408 are coupled in series. Communicative coupling is shown by the arrows in FIG. 4. For example, each of platform 402 and monitoring modules 404, 406, and 408 may include a communications port capable of receiving a plug of one or more suitable wired cables (e.g., shown illustratively by the arrows of FIG. 4). In a further example, platform 402 may include a plurality of communications ports, and each of monitoring modules 404, 406, and 408 may by coupled to respective communications cables, which may respectively couple to communications ports of platform 402, which provides an internal serial connection among monitoring modules 404, 406, and 408. When coupled, as shown by the arrows in FIG. 4, platform 402 and monitoring modules 404, 406, and 408 may form a serial communications bus, over which any of the devices shown may communicate with any or all other devices shown. In some embodiments, the arrows of FIG. 4 may represent wireless coupling (e.g., WiFi standard, BLUETOOTH standard) among platform 402 and monitoring modules 404, 406, and 408. In some embodiments, any or all of platform 402 and monitoring modules 404, 406, and 408 may include chassis or other components which mechanically connect together (e.g., "snap" together using latches, friction mates, and/or flex pivots). In some embodiments, specialized tools (e.g., keys, keyed tools) may be required to couple or uncouple (e.g., insert, remove, plug, unplug) a monitoring module or platform. In some embodiments, biometric identification may be required to couple or uncouple a monitoring module or platform. Under some circumstances, this may prevent unauthorized modification to a patient monitoring system.

Figure 5:
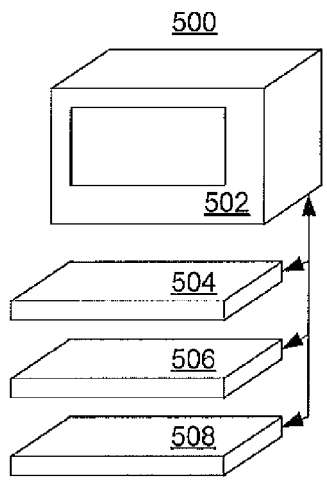
FIG. 5 shows an illustrative parallel arrangement of a platform and monitoring modules, in accordance with some embodiments of the present disclosure.

FIG. 5 shows an illustrative parallel arrangement 500 of a platform 502 and monitoring modules 504, 506, and 508, in accordance with some embodiments of the present disclosure. Arrangement 500 is a parallel arrangement because platform 502 and monitoring modules 504, 506, and 508 are coupled in parallel. Communicative coupling is shown by the arrows in FIG. 5. For example, each of platform 502 and monitoring modules 504, 506, and 508 may include a communications port capable of receiving a plug of one or more suitable wired cables (e.g., shown illustratively by the arrows of FIG. 5). In a further example, platform 502 may include a plurality of communications ports, and each of monitoring modules 504, 506, and 508 may by coupled to respective communications cables, which may respectively couple to communications ports of platform 502. When coupled, as shown by the arrows in FIG. 5, platform 502 and monitoring modules 504, 506, and 508 may form a parallel communications bus, over which any of the devices shown may communicate with any or all other devices shown. In some embodiments, any or all of platform 502 and monitoring modules 504, 506, and 508 may include chassis or other components which mechanically connect together (e.g., "snap" together using latches, friction mates, and/or flex pivots). In some embodiments, the arrows of FIG. 5 may represent wireless coupling (e.g., WiFi standard, BLUETOOTH standard) among platform 502 and monitoring modules 504, 506, and 508.

Figure 6:
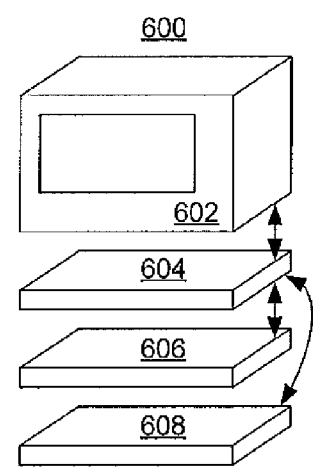
FIG. 6 shows an illustrative branched arrangement of a platform and monitoring modules, in accordance with some embodiments of the present disclosure.

FIG. 6 shows an illustrative branched arrangement 600 of a platform 602 and monitoring modules 604, 606, and 608, in accordance with some embodiments of the present disclosure. Arrangement 600 is a branched arrangement because platform 602 and monitoring modules 604, 606, and 608 are coupled in a combination of serial and parallel. Communicative coupling is shown by the arrows in FIG. 6. For example, each of platform 602 and monitoring modules 604, 606, and 608 may include a communications port capable of receiving a plug of one or more suitable wired cables (e.g., shown illustratively by the arrows of FIG. 6). In a further example, platform 602 may include a plurality of communications ports, and each of monitoring modules 604, 606, and 608 may by coupled to respective communications cables, which may respectively couple to communications ports of platform 602. When coupled, as shown by the arrows in FIG. 6, platform 602 and monitoring modules 604, 606, and 608 may form a serial, parallel, or branched communications bus, over which any of the devices shown may communicate with any or all other devices shown. In some embodiments, any or all of platform 602 and monitoring modules 604, 606, and 608 may include chassis or other components which mechanically connect together (e.g., "snap" together using latches, friction mates, and/or flex pivots). In some embodiments, the arrows of FIG. 6 may represent wireless coupling (e.g., using WiFi standard and hardware, using BLUETOOTH standard and hardware) among platform 602 and monitoring modules 604, 606, and 608. In some embodiments, a branched arrangement may be used when a particular module (e.g., a communications module such as a network module) is configured to communicate directly with one or more other modules. For example, a branched arrangement may be especially useful in cases in which a platform may include limited communication capabilities (e.g., limited number of communications ports, limited support among various communications protocols). In an illustrative example, monitoring module 604 may couple to both monitoring modules 606 and 608 using an Ethernet standard and hardware, while monitoring module 604 may couple to platform 602 using a USB standard and hardware. In a further illustrative example, monitoring module 604 may couple to both monitoring modules 606 and 608 using a USB standard and hardware, while monitoring module 604 may couple to platform 602 using an ethernet standard and hardware.

Figure 7:
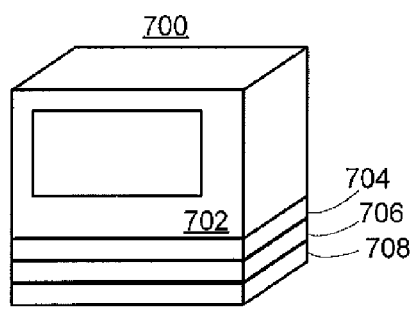
FIG. 7 shows an illustrative stack including a platform and monitoring modules, in accordance with some embodiments of the present disclosure.

FIG. 7 shows an illustrative stack 700 including a platform 702 and monitoring modules 704, 706, and 708, in accordance with some embodiments of the present disclosure. Platform 702 and monitoring modules 704, 706, and 708 may mechanically interlock together to form a single structure (e.g., which may be set on a tabletop or cart as a single device). Electrical connections among platform 702 and monitoring modules 704, 706, and 708 may be integrated into a mechanical coupling or interlock (e.g., using male-female interlocking electrical plugs and sockets). In some embodiments, platform 702 and monitoring modules 704, 706, and 708 may be mounted to a DIN rail, and may be electrically coupled using metal wires arranged in raceways. Any suitable mechanical, electrical, other coupling, or combinations thereof, may be used to create stack 700. In some embodiments, platform 702 and monitoring modules 704, 706, and 708 may be stacked without mechanical interlocking (e.g., simple vertical stacking), and may communicate via suitably coupled cables, wireless paths, optical paths, induction paths (e.g., using near-field inductive communication protocols and hardware) or combinations thereof.

Figure 8:
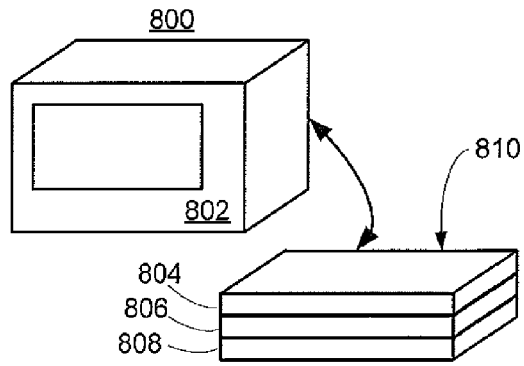
FIG. 8 shows an illustrative platform coupled to a stack of monitoring modules, in accordance with some embodiments of the present disclosure.

FIG. 8 shows an illustrative arrangement 800 in which a platform 802 coupled to a stack 810 of monitoring modules 804, 806, and 808, in accordance with some embodiments of the present disclosure. In some embodiments, platform 802 and monitoring modules 804, 806, and 808 may not form a single stack (e.g., a single structure), but rather a subset may form a stack. In the illustrated embodiment, monitoring modules 804, 806, and 808 form stack 810 while platform 802 is structurally separate. The double tipped arrow in FIG. 8 shows a communicative coupling between platform 802 and stack 810. The shown communicative coupling may include a single cable with terminal connectors, wireless coupling, optical coupling, inductive couplings, any other suitable couplings to any or all modules of stack 810, or any combination thereof. Monitoring modules 804, 806, and 808 may be communicatively coupled to one another (not shown) via wired cables, wireless couplings, optical couplings, inductive couplings, any other suitable couplings, or any combination thereof. In some embodiments, the communicative coupling between platform 802 and stack 810 may include more than one communications path (e.g., three separate cables and connectors for communication with each of monitoring modules 804, 806, and 808).

Figure 9:
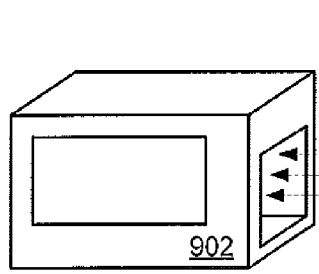
FIG. 9 shows an illustrative platform and monitoring modules which may be inserted, in accordance with some embodiments of the present disclosure.
Figure 10:
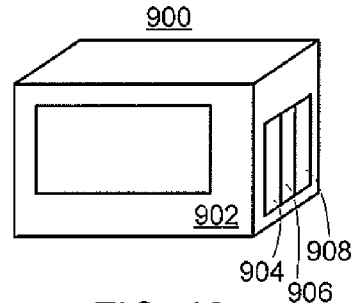
FIG. 10 shows an illustrative platform with monitoring modules inserted therein, in accordance with some embodiments of the present disclosure.

FIG. 9 shows an illustrative platform 902 and monitoring modules 904, 906, and 908 which may be inserted into platform 902, in accordance with some embodiments of the present disclosure. FIG. 10 shows an arrangement 900 including the illustrative platform 902 and monitoring modules 904, 906, and 908 of FIG. 9 with the modules inserted therein (e.g., into corresponding receptacles), in accordance with some embodiments of the present disclosure. Arrangement 900 may include embodiments in which monitoring modules 904, 906, and 908 are "cards" (e.g., separate printed circuit boards (PCBs) with suitable components electrically integrated) which may be inserted into corresponding "slots" (e.g., ports configured to mechanically and electrically connect cards to a communications bus or internal bus) of platform 902. In some embodiments, monitoring modules 904, 906, and 908 may be cartridges, or other sealed units which may mechanically and/or electrically plug into or onto platform 902. Illustrative examples of arrangement 900 include industry standard architecture (ISA) slots and cards, peripheral component interconnect (PCI) slots and cards, accelerated graphics port (AGP) slots and cards, and other suitable communications interface with any suitable number of bits (which may but need not include slots and cards), or any combination thereof. Monitoring modules 904, 906, and 908 may include any suitable communications interface (e.g., standard or non-standard) which may include mechanical couplings (e.g., latches, locks, friction mating, plug/socket connectors), electrical couplings, optical couplings, wireless couplings, other suitable couplings, or any combinations thereof. For example, a 20-pin connector of a monitoring module may be used to electrically and mechanically connect a monitoring module to a platform via a corresponding 20-pin connector of the platform. In some embodiments, monitoring modules 904, 906, and 908 may be inserted into platform 902 by first removing a cover plate or panel (not shown). In some embodiments, a keyed tool may be required to remove the cover plate or panel. In some embodiments, monitoring modules 904, 906, and 908 may each include a chassis which may be secured (e.g., with bolts, latches, friction mates) to a chassis of platform 902.

It will be understood that while various serial, parallel, and branched arrangements are described in the discussion of FIGS. 4-10, any suitable arrangements may be used. For example, in some embodiments, monitoring modules may be mechanically connected in series, but the communications bus may be configured to allow parallel communication among a platform and monitoring modules. In a further example, in some embodiments, monitoring modules may be mechanically connected in parallel, but the communications bus may be configured to allow serial communication among a platform and monitoring modules. In a further example, in some embodiments, monitoring modules may be mechanically connected in a branched arrangement, but the communications bus may be configured to allow serial communication among a platform and monitoring modules. Any suitable communications configuration, mechanical connection, electrical connection, or any other suitable coupling (e.g., optical, wireless) configuration, or any combinations thereof, may be used in accordance with the present disclosure.

It will be understood that while sensor units are not shown in FIGS. 4-10, any of the monitoring modules in FIGS. 4-10 may be parameter modules and may couple to any suitable sensor units.

Figure 11:
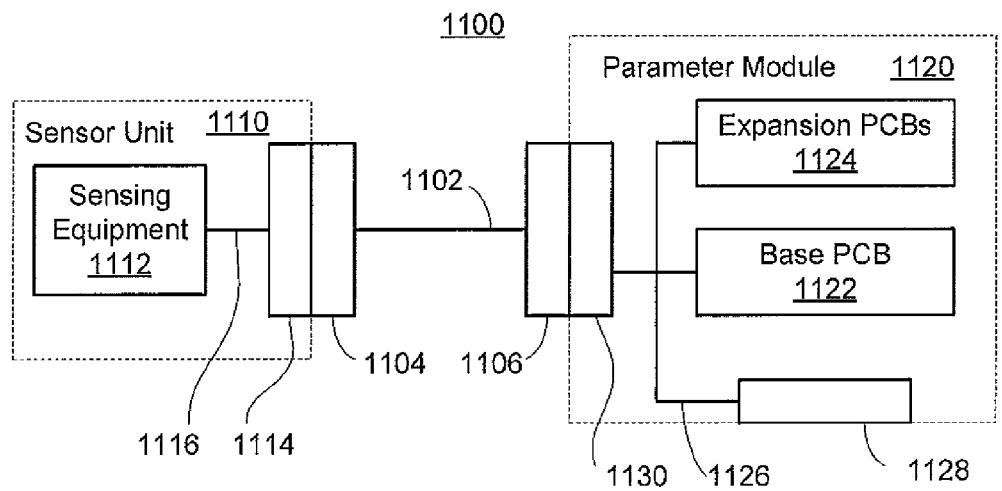
FIG. 11 shows a block diagram of an illustrative sensor unit coupled to a parameter module, in accordance with some embodiments of the present disclosure.

FIG. 11 shows a block diagram 1100 of an illustrative sensor unit 1110 coupled to a parameter module 1120, in accordance with some embodiments of the present disclosure. In the illustrated embodiment, wired cable 1102 with terminal connectors 1104 and 1106 provides communicative coupling between sensor unit 1110 and parameter module 1120, although any suitable communicative coupling may be used in accordance with the present disclosure.

Sensor unit 1110 may include sensing equipment 1112 which may include emitters (e.g., LEDs), photodetectors (e.g., photodiodes), electrodes, thermometric detectors, stimulators (e.g., to provide electrical, acoustic, mechanical or photonic stimulus), processors, memory, communications interfaces, any other suitable equipment, or any combination thereof. Sensing equipment may transmit and receive signals or power via internal bus 1116 providing an electrical connection to connector 1114. Connector 1114 may couple (e.g., male-female electrical plug and socket connection) to connector 1104 of cable 1102, using a suitable connection interface (e.g., a multi-pin connector).

Parameter module 1120 may include base printed circuit board (PCB) 1122 which may include processing equipment, memory, communications interfaces, any other suitable components, or any combination thereof. In some embodiments, parameter module 1120 may be upgraded with one or more expansion PCBs 1124. Expansion PCBs, which are examples of expansion cards, may provide additional functionality, capacity, or both to parameter module 1120, relative to base PCB 1122. In some embodiments, expansion PCBs 1124 may provide any or all the functionality of a utility module such as, for example, an updates module. Base PCB 1122 and expansion PCBs 1124 may be communicatively coupled via internal bus 1126. Internal bus 1126 may couple connectors 1130 and 1128 to base PCB 1122, expansion PCBs 1124, or both. Connector 1130 may couple to connector 1106 of cable 1102, using a suitable connection interface, allowing parameter module 1120 to communicate with sensor unit 1110. Connector 1128 may be configured to couple to a corresponding connector which may be included in a wired cable, another monitoring module, a platform, a sensor, any other suitable device, or any combination thereof. In some embodiments, additional connectors may be coupled to internal bus 1126, and may be configured to connect to additional cables, monitoring modules, platforms, or other devices.

Figure 12:
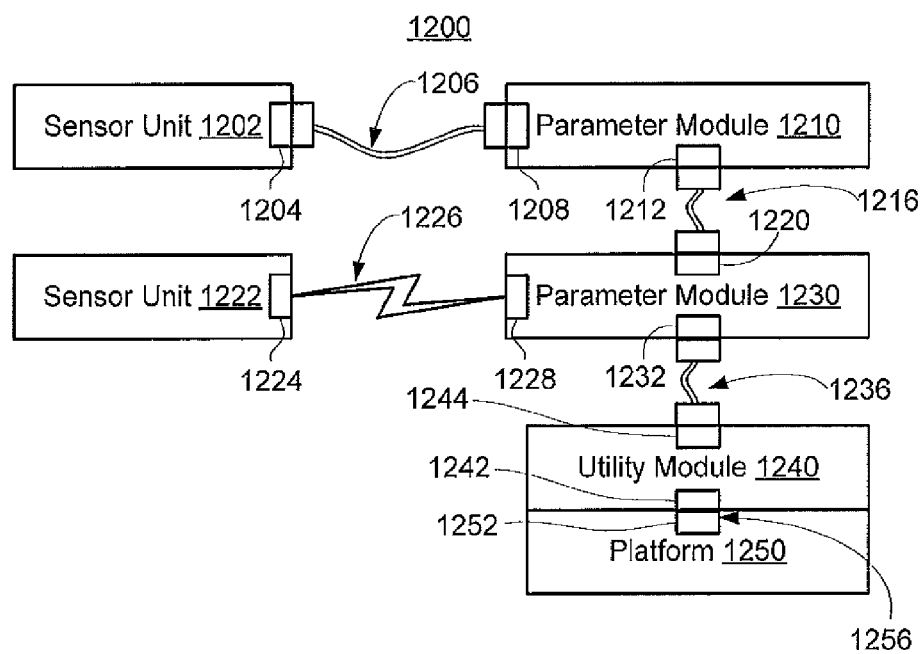
FIG. 12 shows a block diagram of an illustrative patient monitoring system, in accordance with some embodiments of the present disclosure.

FIG. 12 shows a block diagram of an illustrative patient monitoring system 1200, in accordance with some embodiments of the present disclosure. As shown, patient monitoring system 1200 may include sensor units 1202 and 1222, parameter modules 1210 and 1230, utility module 1240 and platform 1250. Sensor unit 1202 may include connector 1204 which may couple to a corresponding connector of cable 1206. Cable 1206 may include a second connector which couples to connector 1208 of parameter module 1210, thus coupling sensor unit 1202 to parameter module 1210. Parameter module 1210 may include connector 1212 which couples to a corresponding connector of cable 1216. Cable 1216 may include a second connector which couples to connector 1210 of parameter module 1230, thus coupling parameter module 1210 to parameter module 1230. Parameter module 1230 may include receiver/transmitter 1228 for wirelessly communicating with sensor unit 1222 (via wireless communication path 1226) which may include a wireless receiver/transmitter 1224. Parameter module 1230 may include connector 1232 which couples to a corresponding connector of cable 1236. Cable 1236 may include a second connector which couples to connector 1224 of utility module 1240, thus coupling parameter module 1230 to utility module 1240. Utility model 1240 may include connector 1242 for directly connecting to connector 1252 of platform 1250 thus forming connection 1256. Although patient monitoring system 1200 provides an illustrative example in accordance with the present disclosure, it will be understood that any suitable arrangement, of any suitable components may be used.

Figure 13:
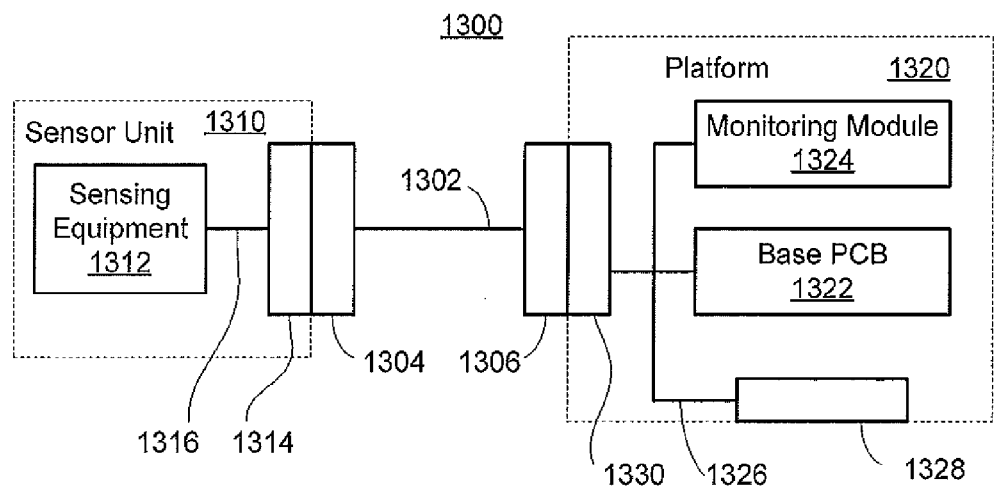
FIG. 13 shows a block diagram of an illustrative sensor unit coupled to a platform, in accordance with some embodiments of the present disclosure.

FIG. 13 shows a block diagram 1300 of an illustrative sensor unit 1310 coupled to a platform 1320, in accordance with some embodiments of the present disclosure. In the illustrated embodiment, wired cable 1302 with terminal connectors 1304 and 1306 provides communicative coupling between sensor unit 1310 and platform 1320, although any suitable communicative coupling may be used in accordance with the present disclosure.

Sensor unit 1310 may include sensing equipment 1312 which may include emitters (e.g., LEDs), photodetectors (e.g., photodiodes), electrodes, thermometric detectors, stimulators (e.g., to provide electrical, acoustic, mechanical or photonic stimulus), processors, memory, communications interfaces, any other suitable equipment, or any combination thereof. Sensing equipment may transmit and receive signals or power via internal bus 1316 providing an electrical connection to connector 1314. Connector 1314 may couple (e.g., male-female electrical plug and socket connection) to connector 1304 of cable 1302, using a suitable connection interface.

Platform 1320 may include base printed circuit board (PCB) 1322 which may include processing equipment, memory, communications interfaces, any other suitable components, or any combination thereof. In some embodiments, a platform may be upgraded with one or more monitoring modules 1324. Monitoring modules, which may be expansion cards, may provide additional functionality, capacity, or both to platform 1320, relative to base PCB 1322. In some embodiments, monitoring modules 1324 may provide any or all the functionality of a utility module such as, for example, an updates module. Base PCB 1322 and monitoring modules 1324 may be communicatively coupled via internal bus 1326. Internal bus 1326 may couple connectors 1330 and 1328 to base PCB 1322, monitoring module 1324, or both. Connector 1330 may couple to connector 1306 of cable 1302, using a suitable connection interface, allowing monitoring module 1320 to communicate with sensor unit 1310. Connector 1328 may be configured to couple to a corresponding connector which may be included in a wired cable, another monitoring module, a platform, a sensor, any other suitable device, or any combination thereof. In some embodiments, additional connectors may be coupled to internal bus 1326, and may be configured to connect to additional cables, monitoring modules, platforms, or other devices.

Figure 14:
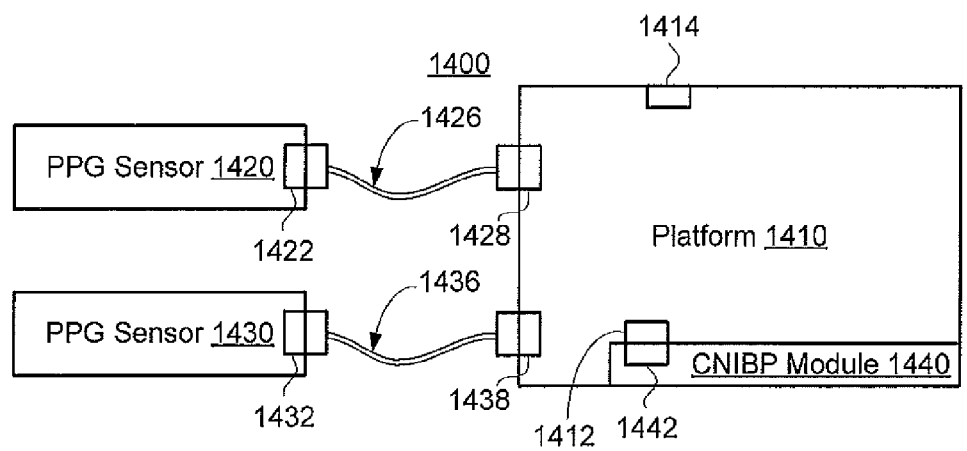
FIG. 14 shows a block diagram of an illustrative patient monitoring system, in accordance with some embodiments of the present disclosure.

FIG. 14 shows a block diagram of an illustrative patient monitoring system 1400 configured as a continuous non-invasive blood pressure (CNIBP) monitor, in accordance with some embodiments of the present disclosure. As shown, patient monitoring system 1400 may include PPG sensors 1420 and 1430, a parameter module such as, for example, CNIBP module 1440, and platform 1410. PPG sensor 1420 may include connector 1422 which may couple to a corresponding connector of cable 1426. Cable 1426 may include a second connector which couples to connector 1428 of platform 1410, thus coupling PPG sensor 1420 to platform 1410. PPG sensor 1430 may include connector 1432 which may couple to a corresponding connector of cable 1436. Cable 1436 may include a second connector which couples to connector 1438 of platform 1410, thus coupling PPG sensor 1430 to platform 1410. Platform 1410 may include connector 1412 which couples to a corresponding connector 1442 of CNIBP module 1440. In the illustrated example of FIG. 14, CNIBP module 1440 is configured to insert into platform 1410. Communicative coupling between CNIBP module 1440 and platform 1410 is provided by connector 1412 which may be a slot with an array of electrical contacts and connector 1442 which may be a portion of a PCB card with an array of corresponding electrical contacts. In some embodiments, a wired cable or wireless coupling may be used to provide communicative coupling between CNIBP module 1440 and platform 1410. Although patient monitoring system 1400 provides an illustrative example of a CNIBP monitor in accordance with the present disclosure, it will be understood that any suitable arrangement, of any suitable components may be used. For example, any of parameters modules 310 discussed in the context of FIG. 3 may be included as a monitoring module inserted into, or otherwise communicatively coupled to, platform 1410.

In some embodiments, platform 1410 may include one or more connectors 1414 which may be used to couple one or more monitoring modules, sensors, any other suitable devices, or any combination thereof. In some embodiments, platform 1410 may be configured to couple to both insertable (e.g., CNIBP module 1440) and non-insertable (e.g., stackable) monitoring modules.

In some embodiments, a patient monitoring system may be imparted increased capabilities (e.g., upgraded) by including one or more monitoring modules. For example, a patient monitoring system may initially include a PPG sensor coupled to the platform. The patient monitoring system may initially be configured to monitor a patient's blood oxygen saturation using a single PPG sensor. Coupling a CNIBP module to the platform may provide the patient monitoring system with the processing capability of using two PPG sensors, placed at different locations on a patient, for CNIBP monitoring (as shown in FIG. 14). The CNIBP module may receive sensor signals (e.g., processed or raw) from the PPG sensors via signal processing circuitry of platform 1410, and process the signals to calculate a blood pressure value.

In some embodiments, a platform may be a standalone device. In some embodiments, a monitoring module may be a standalone device. In some embodiments, a platform may require being coupled to at least one monitoring module to create a device configured for physiological monitoring.

Figure 15:
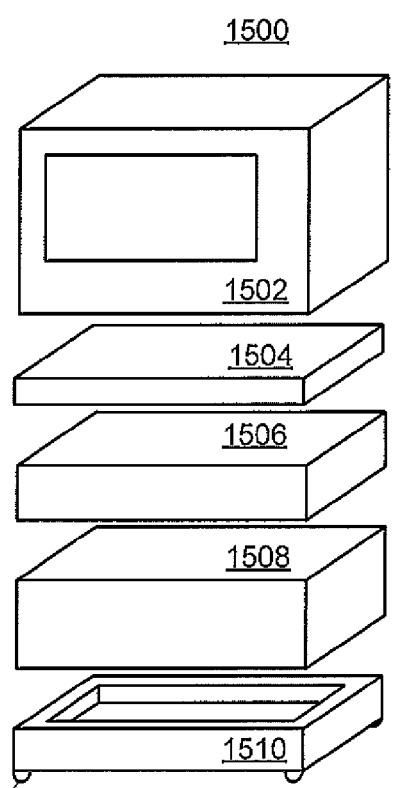
FIG. 15 shows an illustrative platform and several illustrative monitoring modules, in accordance with some embodiments of the present disclosure.
Figure 16:
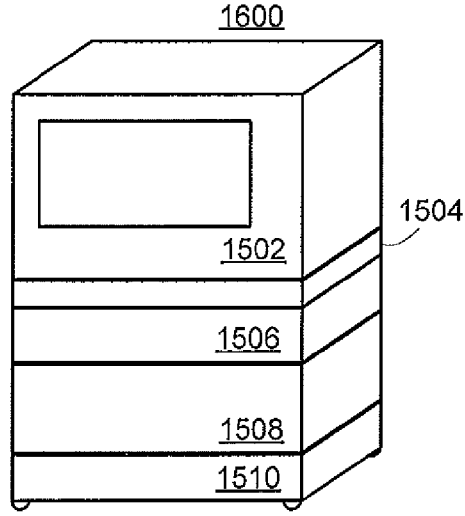
FIG. 16 shows an illustrative stack including a platform and several monitoring modules, in accordance with some embodiments of the present disclosure.

FIG. 15 shows an illustrative collection 1500 of a platform 1502 and several illustrative monitoring modules 1504, 1506, 1508, and 1510, in accordance with some embodiments of the present disclosure. FIG. 16 shows an illustrative stack 1600 including a platform and several monitoring modules, in accordance with some embodiments of the present disclosure.

In some embodiments, monitoring modules which may be relatively heavier, bulkier or otherwise larger may be mounted nearer to the bottom of stack 1600 in order to maintain a relatively lower center of gravity (e.g., to prevent instability, tipping, or damaging smaller/lighter components). Monitoring module 1508 is larger than monitoring module 1506 which is larger than monitoring module 1504, and accordingly, monitoring module 1508 is positioned nearer the bottom of stack 1600 while monitoring module 1504 is positioned nearer the top of stack 1600. In some embodiments, platform 1502 may be mounted at or near the bottom of stack 1600. Any suitable stacking order of platforms and monitoring modules may be used, and in some embodiments, larger monitoring modules may be positioned nearer the top of a stack (e.g., to allow easier user access or increased visibility). As shown in FIG. 16, monitoring module 1510 includes non-skid feet 1512 to provide traction and prevent sliding of stack 1600. Monitoring module 1510 (i.e., the bottom module of illustrative stack 1600) may include casters, legs, rubber feet, slides, ballast, other footing elements, or any combinations thereof to provide tracking, portability, weight, any other suitable functionality, or any combination thereof to stack 1600. Monitoring module 1510 may include a pan, trap, tank or other feature for containing leaks, spills, or debris.

Figure 17:
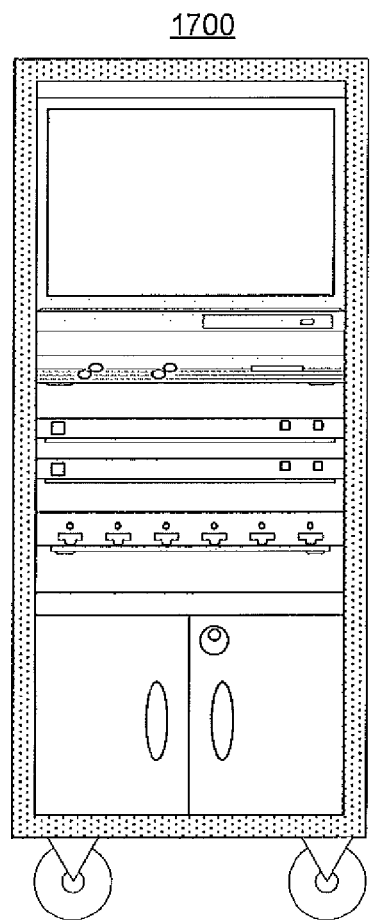
FIG. 17 shows a rack mounted platform and monitoring modules, in accordance with some embodiments of the present disclosure.

FIG. 17 shows an arrangement 1700 of rack-mounted platform and monitoring modules, in accordance with some embodiments of the present disclosure. In some embodiments, arrangement 1700 may include a standard 19-inch rack mount frame, a 23-inch rack mount frame, any other suitable mounting frame, or any combination thereof. In some embodiments, arrangement 1700 may provide structural rigidity, durability, portability (e.g., using swivel casters as shown in FIG. 17), standardization (e.g., for field swapping components, for addition of monitoring modules to an existing system), any other functionality, or any combination thereof. In some embodiments, monitoring modules and platforms may have standard sizes allowing rack mounting of such equipment.

FIG. 18 is a flow diagram 1800 showing illustrative steps for updating a platform, in accordance with some embodiments of the present disclosure.

Step 1802 includes a monitoring module being coupled to a platform (e.g., by a user, by electrical or mechanical actuation of switches) to create a communications bus. Step 1802 may include mechanically connecting the monitoring module to the platform using latches, locking mechanisms, friction mates, screw-down connections, plugs and socket connections, any other suitable mechanical connection, or any combination thereof. Step 1802 may include electrically connecting the monitoring module to the platform to create a communications bus using pin-based electrical connectors, screw-down terminals, blade and socket connectors, any other suitable electrical connection, or any combination thereof. Step 1802 may include wirelessly coupling the monitoring module and the platform to create a communications bus using a wireless communication path (e.g., WiFi standard and hardware, BLUETOOTH standard), optical communications path (e.g., IR communication standard), inductive communications path (e.g., using near-field inductive data transfer), any other suitable non-wired coupling, or any combination thereof. Any suitable coupling may be used to create a communications bus (and possible mechanical connection) in accordance with step 1802.

In some embodiments, step 1802 may be performed automatically by the patient monitoring system, and may include performing a device detection protocol which may include either or both the monitoring module and platform sending device information (e.g., supported communications protocols, supported device functionality, device identification), receiving device information, assigning a device address (e.g., an IP address for networked devices), uploading or downloading device drivers or software add-ons, any other suitable step for device detection, or any combination thereof. In some embodiments, step 1802 may be performed by a user or other suitable entity.

In some embodiments, update information may be received by a monitoring module, as shown by step 1804. In some embodiments, a monitoring module may receive update information from an information source such as another monitoring module, a remote server (e.g., including third party software applications), a website (e.g., a vendor website), an external device coupled to the monitoring module, any other suitable information source which may be communicatively coupled to the monitoring module, or any combination thereof. In some embodiments, a monitoring module may include update information and need not receive update information from a source (i.e., need not perform step 1804). Step 1804 may include the monitoring module receiving a notification over a network, downloading update information from a remote server (e.g., over a wired or wireless network), reading and/or storing update information from a disk or other media (e.g., a DVD), the monitoring module accessing one or more websites for update information, any other suitable steps for receiving update information, or any combination thereof. In some embodiments, step 1804 may be performed periodically such as, for example, a monitoring module performing a weekly download of update information. In some embodiments, step 1804 may be performed by the monitoring module once or aperiodically (e.g., as update information becomes available).

Update information may include software upgrades, device drivers, software applications, patient information, user information, updates themselves, instructions for installing updates, any other suitable information, any other suitable software applications, or any combination thereof. In some embodiments, update information may append or otherwise modify existing information. In some embodiments, update information may include completely new information (e.g., new applications). Updates may include templates (e.g., for processing sensor data), algorithms for calculating additional physiological parameters (e.g., using currently coupled devices or additional equipment), algorithms for calculating additional signal metrics, instructions for interfacing with additional monitoring modules, platforms or sensor, any other suitable type of update, or any combination thereof.

Step 1806 includes a monitoring module preparing an update for a platform. Step 1806 may include a monitoring module translating update information into a format readable by the platform device (e.g., translating from HTML text to Java programming language), redacting update information based on the platform configuration, preparing an update based on a patient monitoring configuration (e.g., a particular combination of monitoring modules and platform), performing any other suitable preparation steps, or any combination thereof. In some embodiments, step 1806 need not be performed, such as situations in which an update does not require preparation by a monitoring module. For example, a monitoring module may upload the update to the platform upon coupling the monitoring module and platform, without performing any preparation steps.

Step 1808 includes a monitoring module uploading an update to a platform using the communications bus. Step 1808 may include the monitoring module compressing or decompressing a file, streaming a file, writing a file, dividing a file into a set of smaller files for transfer,
In some embodiments, step 1808 may include writing the update to removable media (e.g., a DVD, CD, flash USB drive), which may then be inserted into a suitable drive (e.g., of the platform or a media player module coupled to the platform) to allow the platform to download the update.

FIG. 19 is a flow diagram 1900 showing illustrative steps for configuring a patient monitoring system, in accordance with some embodiments of the present disclosure. In some embodiments, a patient monitoring system may be assembled by performing steps 1902 and 1904 (e.g., settings may be configured for an assembled system). In some embodiments, either or both of steps 1902 and 1904 need not be performed (e.g., settings may be configured without the system assembled). Either or both of steps 1902 and 1904, if performed, may be performed a user, the patient monitoring system, or both. Assembling the patient monitoring system may include creating a communications bus among the platform and the one or more monitoring modules of the patient monitoring system.

Step 1902 may include coupling a monitoring module to one or more other monitoring modules (e.g., by a user, by electrical or mechanical actuation of switches). Step 1902 may include using mechanical couplings, electrical communication couplings (e.g., cables with suitable connectors), wireless communication couplings (e.g., suitable transmitters, receivers, and antennas), optical communication coupling, inductive power (e.g., inductive charging) or communication coupling, any other suitable coupling, or any combination thereof. In some embodiments, monitoring modules may be coupled to form a stack.

Step 1904 may include coupling a platform to one or more monitoring modules (e.g., by a user, by electrical or mechanical actuation of switches). Step 1904 may include using mechanical couplings, electrical communication couplings (e.g., cables with suitable connectors), wireless communication couplings (e.g., suitable transmitters, receivers, and antennas), optical communication coupling, inductive power (e.g., inductive charging) or communication coupling, any other suitable coupling, or any combination thereof. In some embodiments, step 1904 may include coupling a platform and one or monitoring modules to form a stack.

Step 1906 includes a monitoring module, platform, or both, configuring a communications bus between a platform and one or more monitoring modules. Configuring the communications bus may include assigning device addresses, configuring a device communications hierarchy (e.g., peer to peer, client-server), determining a communication protocol to use, determining whether devices are coupled in a series, parallel or branched arrangement, configuring the system to serial, parallel, or network communication protocols, performing any other suitable configuration step, or any combination thereof. In some embodiments, step 1906 may include the monitoring module configuring a platform and monitoring module to communicate as peers (i.e., peer to peer communication), in which either device may send information to or receive information (e.g., signals, updates, identification information, any other information) from the other device. In some embodiments, step 1906 may be performed by the platform, monitoring module, or both. In some embodiments, step 1906 may include the monitoring module and the platform performing a "device handshake." A device handshake may include the monitoring module and the platform exchanging information such as capabilities, preferences, status, or other characteristics of each device. In some embodiments, a particular protocol may be used in performing the device handshake such as, for example, exchanging files (e.g., HTML files) in a particular order, exchanging identification codes in a particular order, performing any other suitable information exchange, or any combination thereof. In some embodiments, a device handshake may be used to gather information for performing step 1906.

Step 1908 includes a monitoring module, platform, or both, configuring patient monitoring system settings based at least in part on the configured communications bus of step 1906. Step 1908 may include the monitoring module, platform, or both, determining what data transfer rate is supported by the communications bus, determining device communications hierarchy (e.g., peer-peer, client-server), configuring settings of the patient monitoring system based on any of the foregoing, any other suitable configuration steps, or any combination thereof.

FIG. 20 is a flow diagram showing illustrative steps for specifying system settings, in accordance with some embodiments of the present disclosure.

Step 2002 includes a monitoring module, platform, or both, detecting the platform/module configuration of a patient monitoring system. In some embodiments, step 2002 may include a monitoring module, platform, or both, "pinging" other devices of a patient monitoring system by sending an identifying signal over a communications bus, to which a device coupled to the bus may respond. In some embodiments, step 2002 may include a platform receiving identifying information from one or more monitoring modules (e.g., using an encoder of a monitoring module, or a sensor unit coupled to a parameter module). In some embodiments, step 2002 may include a platform or monitoring module detecting which other devices or types of devices (e.g., monitoring modules, platforms, sensors) are coupled to a patient monitoring system. Step 2002 may include the platform, monitoring module, or both, determining the collective capabilities of the monitoring modules and platform of a patient monitoring system. For example, detecting the configuration may include the platform may determine which modules are coupled to the platform, which physiological parameters the system is capable of monitoring, and which applications may be used for displaying physiological parameters. In some embodiments, step 2002 may include the monitoring module and the platform performing a device handshake. A device handshake may include the monitoring module and the platform exchanging information such as capabilities, preferences, status, or other characteristics of each device. In some embodiments, a particular protocol may be used in performing the device handshake such as, for example, exchanging files (e.g., HTML files) in a particular order, exchanging identification codes in a particular order, performing any other suitable information exchange, or any combination thereof.

Step 2004 includes a monitoring module, platform, or both, providing options to a user based on the detected configuration of step 2004. Options may include options for selecting which monitoring module is currently active or desired to be active, which parameter module physiological signals will be received from, in the memory of which device data is to be stored, which algorithm is to be used in calculating a physiological parameter, any other suitable options which may be provided to a user, or any combination thereof. In some embodiments, a user may select one or more options using a user interface (e.g., of a user interface module or a platform).

Step 2006 includes a monitoring module, platform, or both, specifying patient monitoring system settings based at least in part on selected options of step 2004. Step 2006 may include a monitoring module, platform, or both, specifying how physiological data is to be displayed or recorded (e.g., in memory), specifying which monitoring modules will be used at which times, specifying which monitoring modules will perform which function, any other suitable specification, or any combination thereof. For example, physiological parameter calculations may be performed by a platform, parameter module, or processing module depending upon which option a user selects. In a further example, a user may select an option to use electrical power from a power supply module rather than a power supply of the platform. In a further example, a patient monitoring system may include two separate pulse oximetry modules, and a user may select which pulse oximetry module is to be used at a given time.

FIG. 21 is a flow diagram showing illustrative steps for configuring a patient monitoring system based on device detection, in accordance with some embodiments of the present disclosure.

Step 2102 includes assembling a patient monitoring system (e.g., by a user or by an automated system). Step 2102 may include using mechanical couplings, electrical communication couplings (e.g., cables with suitable connectors), wireless communication couplings (e.g., suitable transmitters, receivers, and antennas), optical communication coupling, inductive power (e.g., inductive charging) or communication coupling, any other suitable coupling, or any combination thereof. In some embodiments, assembling a patient monitoring system may include creating a stack. In some embodiments, for example, the platform and monitoring modules may communicate wirelessly, and step 2102 need not be performed.

Step 2104 includes a monitoring module, platform, or both, detecting a coupled device using a device detection protocol. Step 2104 may include a monitoring module, platform, or both, communicating (e.g., sending, receiving or both) device information (e.g., device identification, supported communications protocols, supported device functionality, device identification), assigning or receiving a device address (e.g., an IP address for networked devices), determining a device class, uploading or downloading device drivers or software add-ons, any other suitable step for device detection, or any combination thereof. In some embodiments, step 2104 may include the monitoring module and the platform performing a device handshake. A device handshake may include the monitoring module and the platform exchanging information such as, for example, capabilities, preferences, status, or other characteristics of each device. In some embodiments, a particular protocol may be used in performing the device handshake such as, for example, exchanging files (e.g., HTML files) in a particular order, exchanging identification codes in a particular order, performing any other suitable information exchange, or any combination thereof.

Step 2106 includes a monitoring module, platform, or both, configuring patient monitoring system settings. In some embodiments, step 2106 may be performed by a monitoring module, platform, or both, based on the device detection of step 2104, although steps 2104 and 2106 may be interchanged in accordance with the present disclosure. Step 2106 may include configuring display settings, data acquisition setting, alarm settings, update settings, communications settings, application settings, any other suitable settings, or any combination thereof.

Any of the illustrative steps of flow diagrams 1800-2100 of FIGS. 18-21 may be suitably omitted, appended, modified, combined with other steps (shown or not shown), rearranged, or otherwise altered in accordance with the present disclosure.

The foregoing is merely illustrative of the principles of this disclosure and various modifications may be made by those skilled in the art without departing from the scope of this disclosure. The above described embodiments are presented for purposes of illustration and not of limitation. The present disclosure also can take many forms other than those explicitly described herein. Accordingly, it is emphasized that this disclosure is not limited to the explicitly disclosed methods, systems, and apparatuses, but is intended to include variations to and modifications thereof which are within the spirit of the following claims.

What is claimed is:

1. A monitoring module comprising:
   a memory storing update information;
   a connection interface;
   a communications bus coupled to the memory and to the connection interface, wherein the connection interface is capable of being mated to a platform, and wherein the monitoring module is configured to update the platform using the communications bus to communicate the update information to the platform; and
   a sensor interface configured to take as input a physiological signal from a sensor coupled to the sensor interface.

2. The monitoring module of claim 1, wherein the monitoring module is a first monitoring module, and wherein the first monitoring module is further configured to update the platform to be capable of communicating with a second monitoring module the platform would otherwise be incapable of communicating with.

3. The monitoring module of claim 1, wherein the monitoring module is a first monitoring module and wherein the first monitoring module and a second monitoring module are coupled to the platform simultaneously.

4. The monitoring module of claim 1, wherein the monitoring module comprises a communications interface coupled to an information source, and wherein the monitoring module is configured to receive the update information from the information source.

5. The monitoring module of claim 4, wherein the communications interface comprises an internal bus, and wherein the information source comprises an expansion card communicatively coupled to the monitoring module using the internal bus.

6. The monitoring module of claim 1 further configured to couple with the platform in a stacking arrangement.

7. A patient monitoring system platform comprising:
   a chassis;
   a user interface;
   a processor coupled to the user interface;
   a communications bus coupled to the processor; and
   a platform connection interface coupled to the communication bus, wherein the chassis is capable of mating with a first monitoring module such that a monitoring module connection interface is coupled to the platform connection interface, and wherein the communications bus is capable of being communicatively extended to other monitoring modules that are coupled in series to one another and to the first monitoring module such that the first monitoring module and a second monitoring module are coupled to the platform connection interface simultaneously, and wherein the processor is configured to process update information received from the first monitoring module and the other monitoring modules to update the patient monitoring system platform.

8. The patient monitoring system platform of claim 7 wherein any of the monitoring modules are removable.

9. The patient monitoring system platform of claim 7 wherein the chassis and platform connection interface are arranged such that mating a monitoring module to the chassis results in a stacked arrangement.

10. The patient monitoring system platform of claim 7 wherein the monitoring modules comprise at least one parameter module.

11. The patient monitoring system platform of claim 7 wherein the monitoring modules comprise at least one utility module.

12. The patient monitoring system platform of claim 7 wherein the processor is configured to process physiological parameter information received from the monitoring modules and the first monitoring module.

13. The patient monitoring system platform of claim 12 wherein the user interface is a display interface configured to display data based at least in part on the physiological parameter information.

14. The patient monitoring system platform of claim 12 further comprising a network interface capable of communicating with a remote monitoring station.

15. A method for updating a platform of a patient monitoring system, the method comprising:
coupling a monitoring module to the platform; and
updating the platform by communicating update information to the platform from the monitoring module using a communications bus, and wherein the updating the platform comprises configuring the platform to communicate with a monitoring module the platform is otherwise unable to communicate with.

16. The method of claim 15, further comprising detecting a device using the communications bus.

17. The method of claim 15, wherein the updating the platform comprises performing a function selected from the group consisting of providing an application for processing an output of a monitoring module, updating software of the platform, updating preference information, updating communication instructions, updating templates of the platform, updating settings of the patient monitoring system, and a combination thereof 18. The method of claim 15, further comprising receiving update information at the monitoring module from an information source.

19. A first monitoring module comprising:
a memory storing update information;
a connection interface; and
a communications bus coupled to the memory and to the connection interface, wherein the connection interface is capable of being mated to a platform, and wherein the first monitoring module is configured to update the platform using the communications bus to communicate the update information to the platform, and wherein the first monitoring module and a second monitoring module are coupled to the platform simultaneously.

* * * * *